(12) United States Patent
Farmer et al.

(10) Patent No.: US 11,160,586 B2
(45) Date of Patent: Nov. 2, 2021

(54) ANCHORING DEVICE WITH EXTENDED TABS

(71) Applicant: Zimmer Biomet Spine, Inc., Westminster, CO (US)

(72) Inventors: Heidi Farmer, Lafayette, CO (US); Jared Parker, Denver, CO (US); Randall G. Mast, Denver, CO (US)

(73) Assignee: Zimmer Biomet Spine, Inc., Westminster, CO (US)

( * ) Notice: Subject to any disclaimer, the term of this patent is extended or adjusted under 35 U.S.C. 154(b) by 75 days.

(21) Appl. No.: 16/387,222

(22) Filed: Apr. 17, 2019

(65) Prior Publication Data

US 2019/0343558 A1 Nov. 14, 2019

Related U.S. Application Data

(60) Provisional application No. 62/669,192, filed on May 9, 2018.

(51) Int. Cl.
*A61B 17/70* (2006.01)
*A61B 90/00* (2016.01)

(52) U.S. Cl.
CPC ........ *A61B 17/708* (2013.01); *A61B 17/7032* (2013.01); *A61B 17/7082* (2013.01); *A61B 2090/037* (2016.02)

(58) Field of Classification Search
CPC .............. A61B 17/708; A61B 17/7076; A61B 17/7077; A61B 17/7079
See application file for complete search history.

(56) References Cited

U.S. PATENT DOCUMENTS

| 7,497,869 B2 | 3/2009 | Justis |
| 7,927,360 B2 | 4/2011 | Pond et al. |

(Continued)

FOREIGN PATENT DOCUMENTS

| DE | 112019001925 | 1/2021 |
| EP | 2356944 | 8/2011 |

(Continued)

OTHER PUBLICATIONS

"International Application Serial No. PCT US2019 027941, International Search Report dated Jul. 9, 2019", 7 pages.

(Continued)

*Primary Examiner* — Jan Christopher L Merene
(74) *Attorney, Agent, or Firm* — Schwegman Lundberg & Woessner, P.A.

(57) ABSTRACT

An anchor can be coupleable to a bone, where the anchor includes a head, a shank, a first extension, and a second extension. The head can include a distal head portion and a proximal head portion, where the proximal head portion can be open at a proximal end of the head. The shank can extend distally from the distal head portion, where the shank including a threaded portion configured to engage the bone. The second extension can be opposing the first extension, and the second extension can include a second proximal support coupled to a second end of a first elongate portion, where a first proximal support can extend transverse to the longitudinal axis, and the first proximal support portion and the second proximal support portion can be separated in a first condition and can be engaged to transfer forces there between in a second.

3 Claims, 26 Drawing Sheets

(56) References Cited

U.S. PATENT DOCUMENTS

| | | |
|---|---|---|
| 7,967,821 B2 | 6/2011 | Sicvol et al. |
| 8,236,032 B2 | 8/2012 | Ramsay et al. |
| 8,262,662 B2 | 9/2012 | Beardsley et al. |
| 8,333,770 B2 | 12/2012 | Hua |
| 8,388,659 B1 | 3/2013 | Lab et al. |
| 8,439,923 B2 | 5/2013 | Won et al. |
| 8,523,913 B2 | 9/2013 | Jackson |
| 8,603,094 B2 | 12/2013 | Walker et al. |
| 8,747,407 B2 | 6/2014 | Gorek |
| 8,764,754 B2 | 7/2014 | Butler et al. |
| 8,852,238 B2 | 10/2014 | Nazeck et al. |
| 8,858,605 B1 | 10/2014 | Glatzer et al. |
| 8,932,210 B2 | 1/2015 | Woods |
| 9,011,449 B1 | 4/2015 | Cochran |
| 9,125,694 B2 | 9/2015 | Butler et al. |
| 9,198,692 B1* | 12/2015 | Doose ................ A61B 17/7086 |
| 9,216,040 B2 | 12/2015 | Anderson et al. |
| 9,220,543 B2 | 12/2015 | Walker et al. |
| 9,364,265 B2 | 6/2016 | Ramsay et al. |
| 9,408,716 B1 | 8/2016 | Reitblat et al. |
| 9,603,628 B2 | 3/2017 | Butler et al. |
| 2006/0149238 A1 | 7/2006 | Sherman et al. |
| 2008/0082103 A1* | 4/2008 | Hutton ................ A61B 17/708 606/272 |
| 2010/0174325 A1* | 7/2010 | Won .................. A61B 17/7037 606/305 |
| 2011/0202095 A1* | 8/2011 | Semler .............. A61B 17/8605 606/308 |
| 2013/0012999 A1 | 1/2013 | Petit |
| 2013/0053896 A1 | 2/2013 | Voyadzis |
| 2013/0103096 A1 | 4/2013 | Miller |
| 2014/0031874 A1 | 1/2014 | Kucharzyk et al. |
| 2015/0066042 A1 | 3/2015 | Cummins et al. |
| 2015/0173809 A1 | 6/2015 | Bechtel et al. |
| 2016/0008034 A1* | 1/2016 | Stokes ................ A61B 17/708 606/278 |
| 2016/0045233 A1 | 2/2016 | Anderson et al. |
| 2016/0113685 A1* | 4/2016 | Ishii .................. A61B 17/7037 606/266 |
| 2016/0143674 A1 | 5/2016 | Harris |
| 2016/0235450 A1 | 8/2016 | Walker et al. |
| 2016/0345952 A1 | 12/2016 | Kucharzyk et al. |
| 2017/0079696 A1* | 3/2017 | Walker ................ A61B 17/708 |
| 2017/0238975 A1 | 8/2017 | Doose et al. |

FOREIGN PATENT DOCUMENTS

| | | |
|---|---|---|
| EP | 2868282 | 5/2015 |
| WO | WO-2017027694 A1 | 2/2017 |
| WO | 2019217045 | 11/2019 |

OTHER PUBLICATIONS

"International Application Serial No. PCT US2019 027941, Written Opinion dated Jul. 9, 2019", 12 pages.

"International Application Serial No. PCT US2019 027941, International Preliminary Report on Patentability dated Nov. 19, 2020", 12 pages.

* cited by examiner

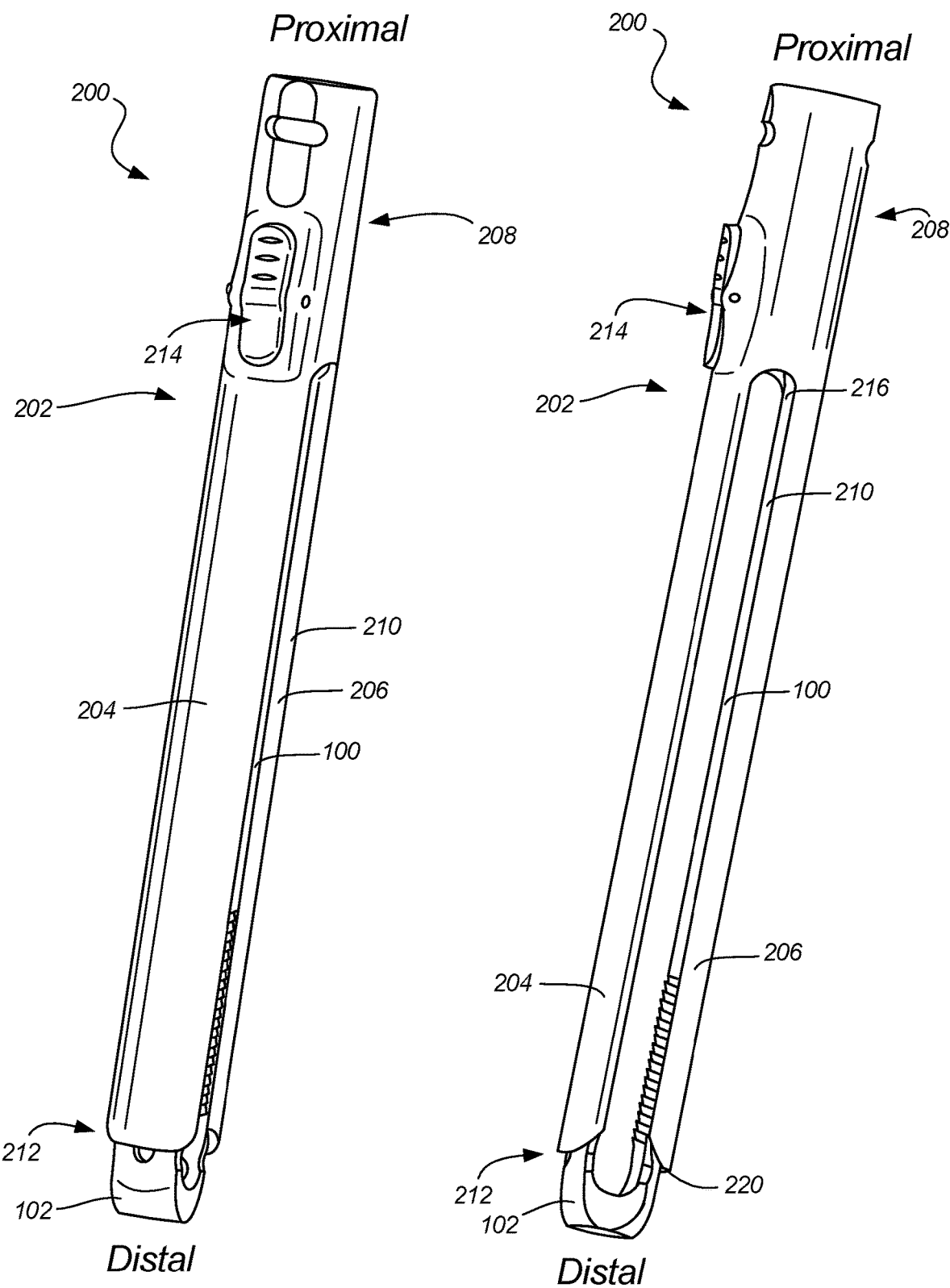
FIG. 4A  FIG. 4B

ANCHORING DEVICE WITH EXTENDED TABS

CLAIM OF PRIORITY

This application claims the benefit of U.S. Provisional Patent Application Ser. No. 62/669,192, filed on May 9, 2018, the benefit of priority of which is claimed hereby, and which is incorporated by reference herein in its entirety.

BACKGROUND

Orthopedic devices such as rods, plates, tethers, staples, and other devices can be used in various spinal procedures to correct abnormalities (e.g., scoliosis) or to address injuries (e.g., vertebral fracture). In some spinal procedures, anchors and rods can be secured along a spinal column between one or more vertebrae to stabilize a region of the spine. Some surgical procedures performed on the spinal column using such devices have become less invasive. However, some special parts used in minimally-invasive spinal procedures can increase the difficulty of the installation procedure.

OVERVIEW

In certain procedures the inventors have found extended tab pedicle screws to be beneficial and improve the speed at which a surgeon can perform the procedure. However, traditional extended tab pedicle screws suffer from instability at the proximal end of the tabs, which can negatively impact the surgeon's ability to take advantage of the benefits provided by the extensions. Accordingly, a solution has been developed where the proximal end of the extensions each include mating features that engage the opposing extension to form a semi-rigid, but separable, structure on the proximal end of the extended tab pedicle screw construct. The mating feature can take on different shapes, but each mating structure can be intended to stabilize the proximal end of the extended tab pedicle screw construct. This stabilization can help prevent pinching inward of the extended tabs, which can hinder tool insertion and visibility, while still allowing for the tabs to be split, which allows for a rod to be easily passed down between the extensions.

In one example, an anchor can be coupleable to a bone, where the anchor can include a head, a shank, a first extension, and a second extension. The head can include a distal head portion and a proximal head portion, where the proximal head portion can be open at a proximal end of the head. The shank can extend distally from the distal head portion, and the shank can include a threaded portion configured to engage the bone. The first extension can include a first breakaway portion coupling the first extension to the proximal head portion, where the first extension can be separable from the head at the first breakaway portion. The first extension can include a first elongate portion extending from a first end proximate the first breakaway portion to a second end along a longitudinal axis of the anchor, where the first elongate portion can include a length sufficient to extend the second end outside an incision when the shank is engaged in the bone. The first extension can include a first proximal support that can be coupled to the second end of the first elongate portion, where the proximal support can extend transverse to the longitudinal axis. The second extension can oppose the first extension, and the second extension can include a second breakaway portion that can couple the second extension to the proximal head portion, where the second extension can be separable from the head at the second breakaway portion. The second elongate portion can extend from a first end proximate the first breakaway portion to a second end along a longitudinal axis of the anchor. The first elongate portion can include a length sufficient to extend the second end outside an incision when the shank is engaged in the bone. The second extension can include a second proximal support coupled to the second end of the first elongate portion, where the proximal support can extend transverse to the longitudinal axis, and where the first proximal support portion and the second proximal support portion can be separated in a first condition and engaged to transfer forces there between in a second condition. The first and second extensions can include a threaded portion on internal faces of the first and second extensions, where the threaded portion can extend distally from the first and second extensions into the head portion.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 4A illustrates an isometric front view of an anchor and sleeve assembly, in accordance with at least one example of this disclosure.

FIG. 4B illustrates an isometric side view of an anchor and sleeve assembly, in accordance with at least one example of this disclosure.

DETAILED DESCRIPTION

Figure 1:
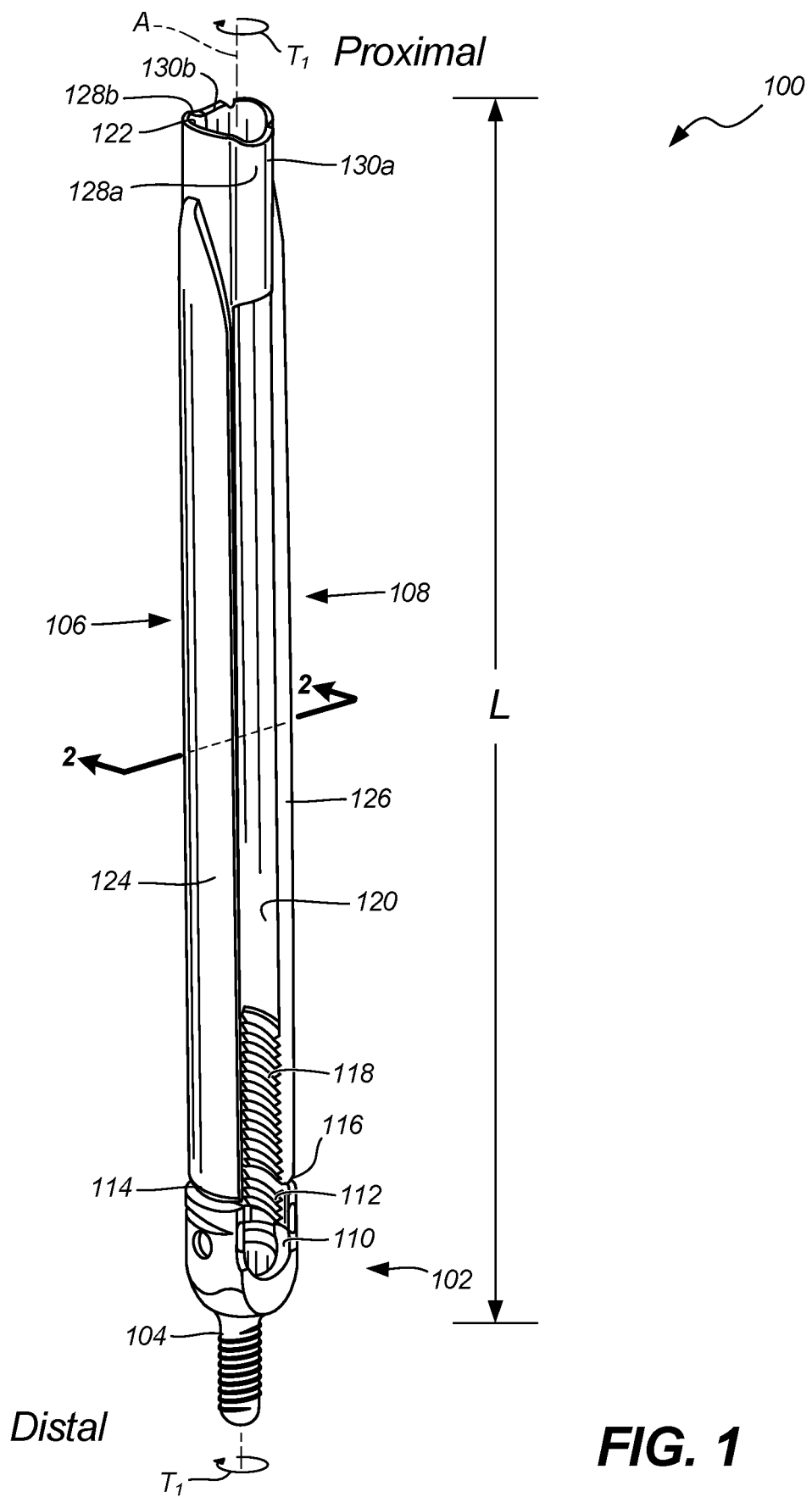
FIG. 1 illustrates an isometric view of an anchor with extended tabs, in accordance with at least one example of this disclosure.

Bone anchors can be used together with connecting members (such as rigid and semi-rigid rods) to straighten a region of a human spine to address an abnormality (e.g., scoliosis), to stabilize a spine following an injury (e.g., fractured vertebrae), or to address degeneration of the spine caused by disease. In minimally invasive spinal procedures to address these issues, multiple small incisions can be made to form multiple small cavities near individual vertebrae. A large amount of the procedure is performed through manipulation of instruments and components extending through the small surgical cavities using special instruments that are able to be manipulated from outside of the cavities. For example, anchors are commonly driven into vertebrae, where the anchors include extended tabs rigidly coupled to the anchors and having a length sufficient to extend outside of the cavity so that the anchors (and components engaging the anchors) can be manipulated from outside of the cavities. Because the extended tabs comprise a length sufficient to extend through the cavities, they often must be separable from the heads of the anchors (which remain secured to vertebrae). Further, because the extensions often need to receive a connecting member and a closure top, the extensions must often be of a quantity of at least two to allow threading of the closure top into the head of the anchor and to provide a slot to reduce and retain the connecting member.

Some designs include two extensions each coupled to the head of the anchor at a breakaway portion, where each extended tab can be individually bent to allow separation of the extension from the head at the breakaway portions. This design requires relative movement of the extended tabs for separation. However, the extended tabs must also be rigid enough to transfer forces between the tabs. Sometimes the forces must be transferred from a portion of the extended tabs external to the cavity to a portion of the extended tabs into the cavity and ultimately to the head and/or shank of the anchor. To allow individual separation of the extended tab while also allowing transfer of forces and torques of the tabs without unintended separation of the extension from the head, extensions are often formed together at a proximal end of the extensions. In these cases, the extensions must be separated or broken away from each other in order to facilitate breaking off each extension from the pedicle screw. Separation can increase a risk of material being lost into a cavity and adds another step to the procedure.

This disclosure addresses these problems with extended tabs by including support pieces that do not require separation. More specifically, to solve the problem of allowing transfer of torque and forces between the extensions without requiring separation of the extended tabs, while helping to avoid unwanted pinching in of the extended tabs during the procedure, this disclosure proposes proximal supports extending from a proximal end of each extended tab that are not formed together (or are separate). The proximal supports can be engaged with each other to allow transfer of torque and/or forces between the supports (and therefore between the extended tabs); however, the supports do not require separation, which can help reduce debris produced during a procedure and can save the step of separation of the extended tabs, which can save time during the procedure. This disclosure also addresses the problem of allowing individual separation of the extended tab while allowing transfer of forces and torques of the tabs without unintended separation of the extension from the head by providing a sleeve couplable to the anchor where the sleeve can transfer forces directly to and from the head of the anchor instead of to and from the extended tabs.

FIG. 1 illustrates an isometric view of anchor 100 with extended tabs, in accordance with at least one example of this disclosure. Anchor 100 can include head 102, shank 104, and extensions 106 and 108. Head 102 can include channel 110, head threading 112, and breakaway portions 114 and 116. Extensions 106 and 108 can include extension threading 118, channels 120 (only 1 visible in FIG. 1), and proximal opening 122. Extension 106 can include elongate portion 124 and proximal supports 128a and 128b. Extension 108 can include elongate portion 126 and proximal supports 130a and 130b. Also shown in FIG. 1 are axis A, length L, torque T1, and orientation indicators Proximal and Distal.

The components of anchor 100 can be comprised of rigid and semi-rigid materials such as metals, plastics, composites, and the like. In some examples, anchor 100 can be comprised of bio-compatible materials, such as stainless steel, titanium, and the like. In some examples, anchor 100 can be comprised of only one material and can be comprised of multiple materials in other examples.

Head 102 can be a head of anchor 100 where head 102 can be coupled to shank 104 at a distal portion of head 102 with shank 104 extending distally therefrom and where axis A can be a central axis for head 102 and shank 104. In other examples, shank 104 can deviate from axis A at various angles. Shank 104 can be a threaded shank or screw including male threads configured to engage bone, such as a relatively coarse thread pattern. In some examples, shank 104 can be configured to threadably secure to a vertebra of a spine of a human. Shank 104 can be an integral component to head 102 in some examples, coupled to a distal portion of head 102. In other examples, shank 104 can be a portion of a fastener that is a separate component from head 102 and can be disposed within a bore of head 102 and configured to be retained therein.

Channel 110 of head 102 can be generally U-shaped in some examples, and can be configured to receive a connecting member (such as a connecting rod or wire) therethrough. In some examples, head 102 can have flat sides and one or more tool interfaces, as discussed further below. Breakaway portions 114 and 116 can be a portion of anchor 100 coupling head 102 to extensions 106 and 108, where breakaway portions 114 and 116 can have a thickness that is smaller than a thickness of head 102 or extensions 106 and 108 that surrounds breakaway portions 114 and 116. The reduced thickness of breakaway portions 114 and 116 can facilitate separation and removal of extensions 106 and 108 from head 102, as discussed further below.

Head threading 112 can be a female threaded portion within channel 110 of head 102. Head threading 112 can be aligned with extension threading 116 and can be of the same thread type (spacing, pitch, etc.) as extension threading 112. In some examples, head threading 112 can be relative fine threading (such as machine-type threading) configured to receive a component having male threading, such as a closure top or set screw configured to retain a connecting member or rod.

Extensions 106 and 108 can include elongate portion 124 and elongate portion 126, respectively, which can be substantially longitudinal bodies extending substantially proximally from head 102 and substantially parallel to axis A. In some examples, elongate portions 124 and 126 can have a length L sufficient to extend a proximal end of extensions 106 and 108 outside an incision when shank 104 is engaged in a bone. Together, elongate portions 124 and 126 can form an incomplete hollow cylinder separated by channels 120. Channels 120 can be slots between elongate portions 124 and 126 that substantially align with channels 110 of head 102. Extensions 106 and 108 can be coupled to head 102 by break off portions 114 and 116, as noted above. In some examples, extension threading 118 can be relative fine threading (such as machine-type threading) configured to receive a component having male threading, such as a closure top.

Proximal supports 128a and 128b can extend substantially orthogonally (or transversely) from a proximal portion of elongate portion 124 and proximal supports 130a and 130b can extend substantially orthogonally (or transversely) from a proximal portion of elongate portion 126. Proximal supports 128a and 128b and proximal supports 130a and 130b can extend toward each other in some examples, such that terminations of proximal support 128a and proximal support 130a can be adjacent and separated in a first condition and can engage to transfer forces and/or torques there between in a second condition.

Extensions 106 and 108 can also include proximal opening 122 formed by elongate portion 124, elongate portion 126, proximal support portions 128a and 128b, and proximal support portions 130a and 130b. In some examples, proximal opening 122 can be sized to receive a fastener therethrough, where the fastener can be passed distally between extension 106 and 108 to extension threading 118.

In operation of some examples, once a patient's spinal region (and specifically a vertebra) is prepared (as discussed below), anchor 100 can be extended into an incision and aligned with a portion of the vertebra (for example a guide bore) configured to receive shank 104. In this condition, proximal support portions 128a and 128b can be adjacent to proximal support portions 130a and 130b but may not be in contact in some examples. In other examples, proximal support portions 128a and 128b and proximal support portions 130a and 130b can be in contact, but can be entirely separate components.

Once shank 104 is engaged with the bore of the vertebra, torque T1 can be applied to head 102 about axis A using a tool. When torque T1 is applied to head 102, Torque T1 can be transferred proximally up extensions 106 and 108 and can then be transferred between extensions 106 and 108 through proximal support portions 128a and 128b and proximal support portions 130a and 130b. For example, torque T1 can be transferred between support portions 128a and 130a and can be transferred between support portions 128b and 130b, helping to prevent pinching in of extensions 106 and 108 during driving of shank 104 into bone.

Once shank 104 is secured into the vertebra, a connecting member can be passed through slots 120 between extensions 106 and 108 and can be reduced down through channels 120 and into channel 110 of head 102. At a later time, or during reduction, a closure top (or other fastener) can be pass through proximal opening 122 and can be threaded into extension threading 118 and down to head threading 112 and into channel 110 of head 102 to retain the connecting member.

During reduction, especially when using a set screw to reduce a rod through extensions 106 and 108, forces and torques can be applied to extensions 106 and 108 when torque T1 is applied to the set screw. This torque (or the resulting forces) can be transferred between support portions 128a and 130a and can be transferred between support portions 128b and 130b to reduce flexing of tabs 106 and 108 at breakaway portions 114 and 116. Breakaway portions 114 and 116 can be of a sufficient thickness to transfer forces and torques between extensions 106 and 108 and head 102 during reduction without causing separation of extensions 106 and 108 from head 102. Also, because proximal support portions 128a and 130a engage each other and 128b and 130b engage each other during transfer of these forces, movement of elongate portions 124 and 126 relative to head 102 is reduced, helping to prevent unwanted breakaway of extensions 106 and 108 during the process of driving shank 104 into bone.

Because proximal support portions 128a and 128b and proximal support portions 130a and 130b are configured to be separate but engageable, proximal support portions 128a and 128b and proximal support portions 130a and 130b allow for the transfer of torque and forces there between without requiring proximal support portions 128a and 128b to be formed together. Because proximal support portions 128a and 128b do not have to be separated from 130a and 130b, less debris may be produced and a step of separation of extended tabs 106 and 108 can be eliminated, which can save time during the procedure.

Figure 2A:
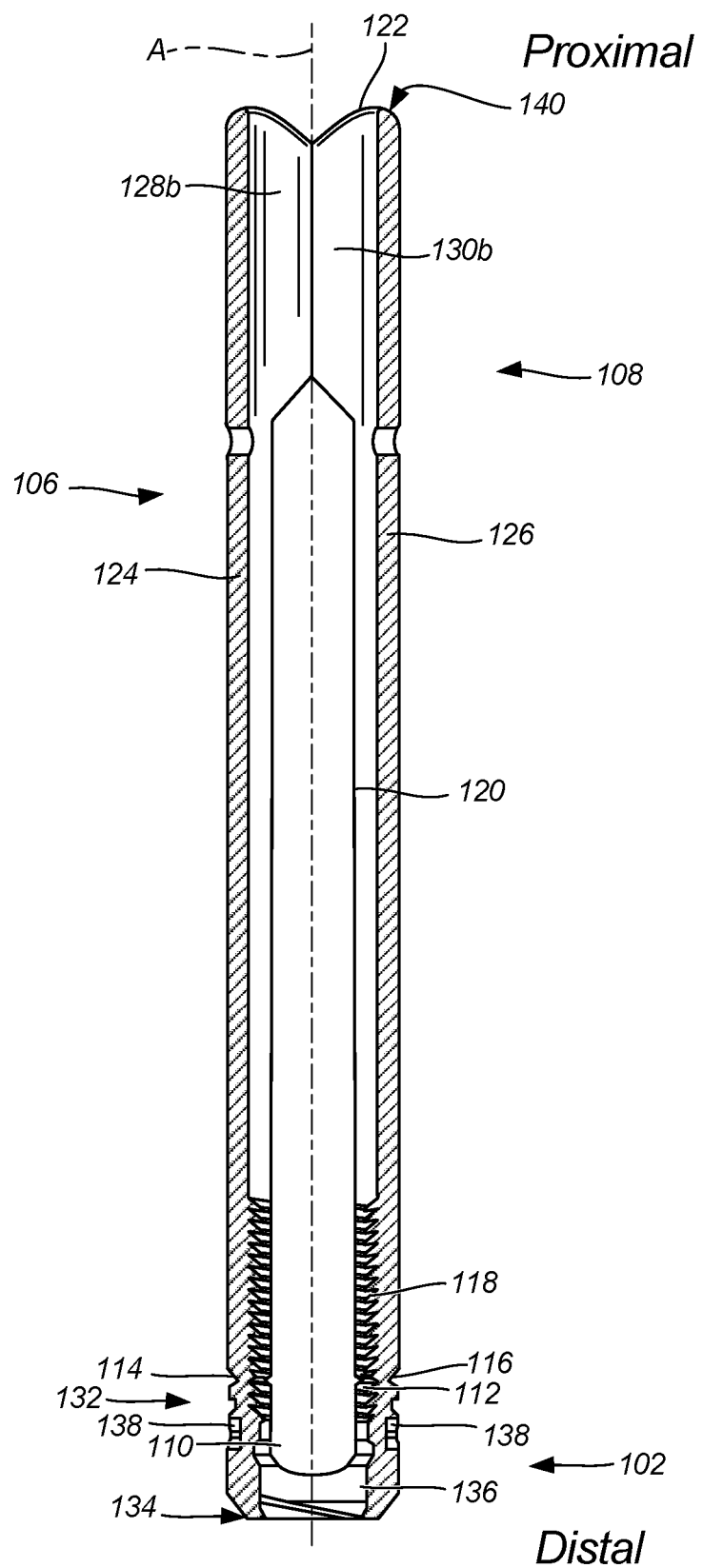
FIG. 2A illustrates cross-sectional view of an anchor with extended tabs across section 2-2 of FIG. 1, in accordance with at least one example of this disclosure.
Figure 2B:
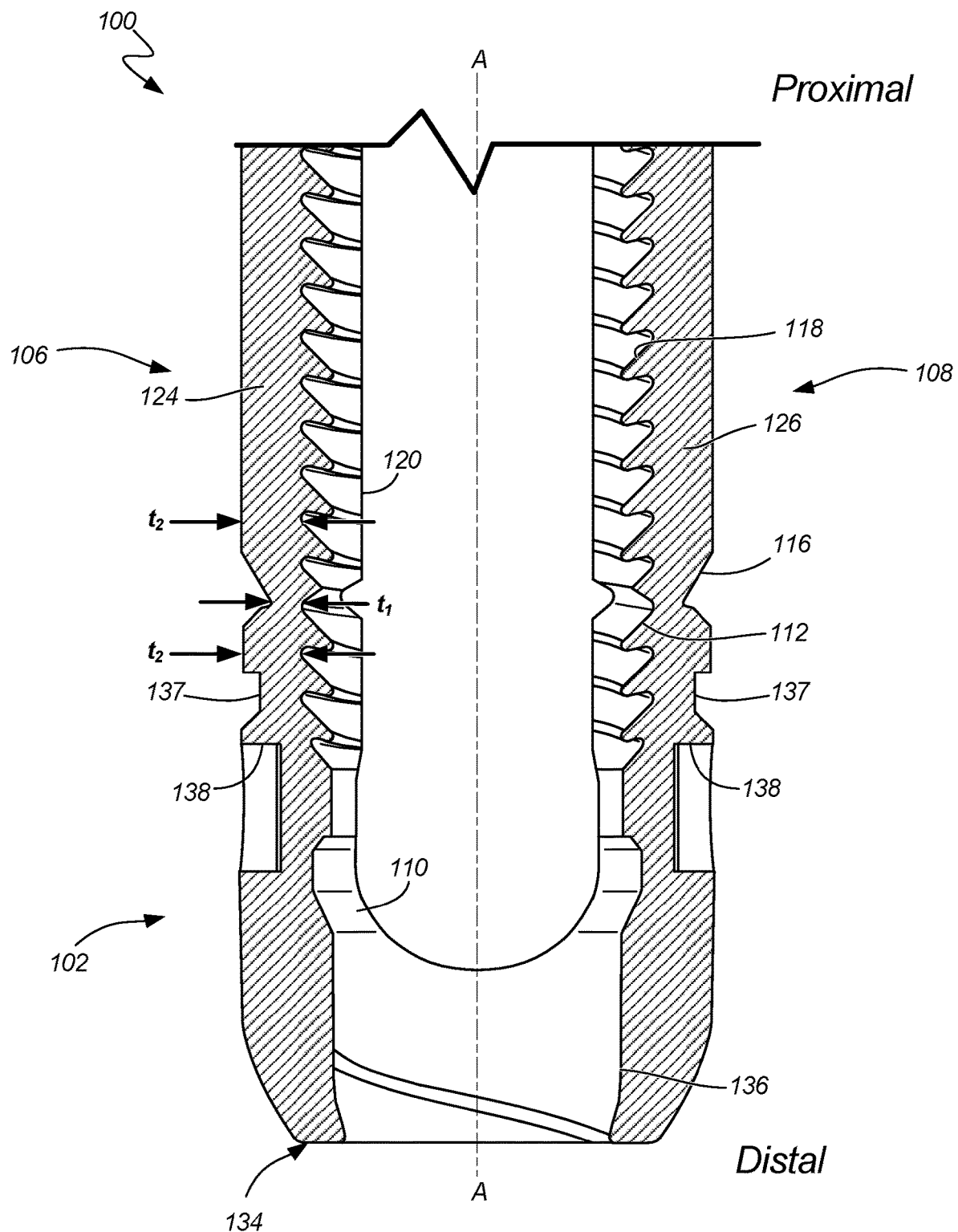
FIG. 2B illustrates cross-sectional view of a portion of an anchor with extended tabs across section 2-2 of FIG. 1, in accordance with at least one example of this disclosure.

FIG. 2A illustrates cross-sectional view of anchor 100 across section 2-2 of FIG. 1, in accordance with at least one example of this disclosure. FIG. 2B illustrates cross-sectional view of a portion of anchor 100 across section 2-2 of FIG. 1, in accordance with at least one example of this disclosure. FIGS. 2A and 2B are discussed below concurrently.

Anchor 100 can include head 102 and extensions 106 and 108. Head 102 can include channel 110, head threading 112, breakaway portions 114 and 116, proximal head portion 132, distal head portion 134, shank bore 136, and tool interface 138. Extensions 106 and 108 can include extension threading 118, channels 120 (only 1 visible in FIGS. 2A and 2B), and proximal opening 122. Extension 106 can include elongate portion 124 and extension 108 can include elongate portion 126. Extension 106 can include proximal supports 128a and 128b (only proximal support 128b is visible in FIG. 2A) and extension 108 can include proximal supports 130a and 130b (only proximal support 130b is visible in FIG. 2A). Extensions 106 and 108 can terminate at proximal extension portion 140. Also shown in FIGS. 2A and 2B are thickness t1, thickness t2, axis A, and orientation indicators Proximal and Distal.

Anchor 100 of FIGS. 2A and 2B can be consistent with anchor 100 of FIG. 1; however, FIGS. 2A and 2B show additional details of anchor 100. For example, FIG. 2 shows a position of proximal head portion 132 near where head portion couples to extensions 106 and 108 via breakaway portions 114 and 116. Distal head portion 134 can be located near a distal termination of head 102.

Shank bore 136 can be an internal central bore of head 102 open to a proximal end of proximal portion 134 of head 102. Shank bore 136 can be configured and sized to receive and retain an anchor or shank (such as shank 102 of FIG. 1) therein. In some examples, shank bore 136 can be sized to prevent rotation of the shank relative to head 102.

FIGS. 2A and 2B also show rim interface 137 of head 102. Rim interface 137 can be a notch, slot, recess, and the like in opposing sides of head 102. Rim interface 137 can be sized to receive a tab or projection at a distal portion of a sleeve to retain the sleeve on anchor 100.

FIGS. 2A and 2B also show tool interface 138 of head 102. Tool interface 138 can be a notch, slot, recess, and the like in opposing sides of head 102. Tool interface 138 can be sized to receive a tool or portion of a tool therein. FIGS. 2A and 2B also show how breakaway portions 114 and 116 can have a reduced thickness. For example, breakaway portion 114 can have thickness t1, as shown in FIG. 2B and adjacent portions of head 102 and extension 106 can have thickness t2, which can be larger than thickness t1. This can allow for extension 106 to be bent at breakaway portion 114, allowing for separation of extension 106 from head 102 at breakaway portion 114. In other examples, thickness t1 can be the same thickness as thickness t2. In some other example, thickness t1 can be smaller than thickness t2, but can have a radially inner diameter that is the same as that of threading 118, noted at thickness t2.

Figure 3:
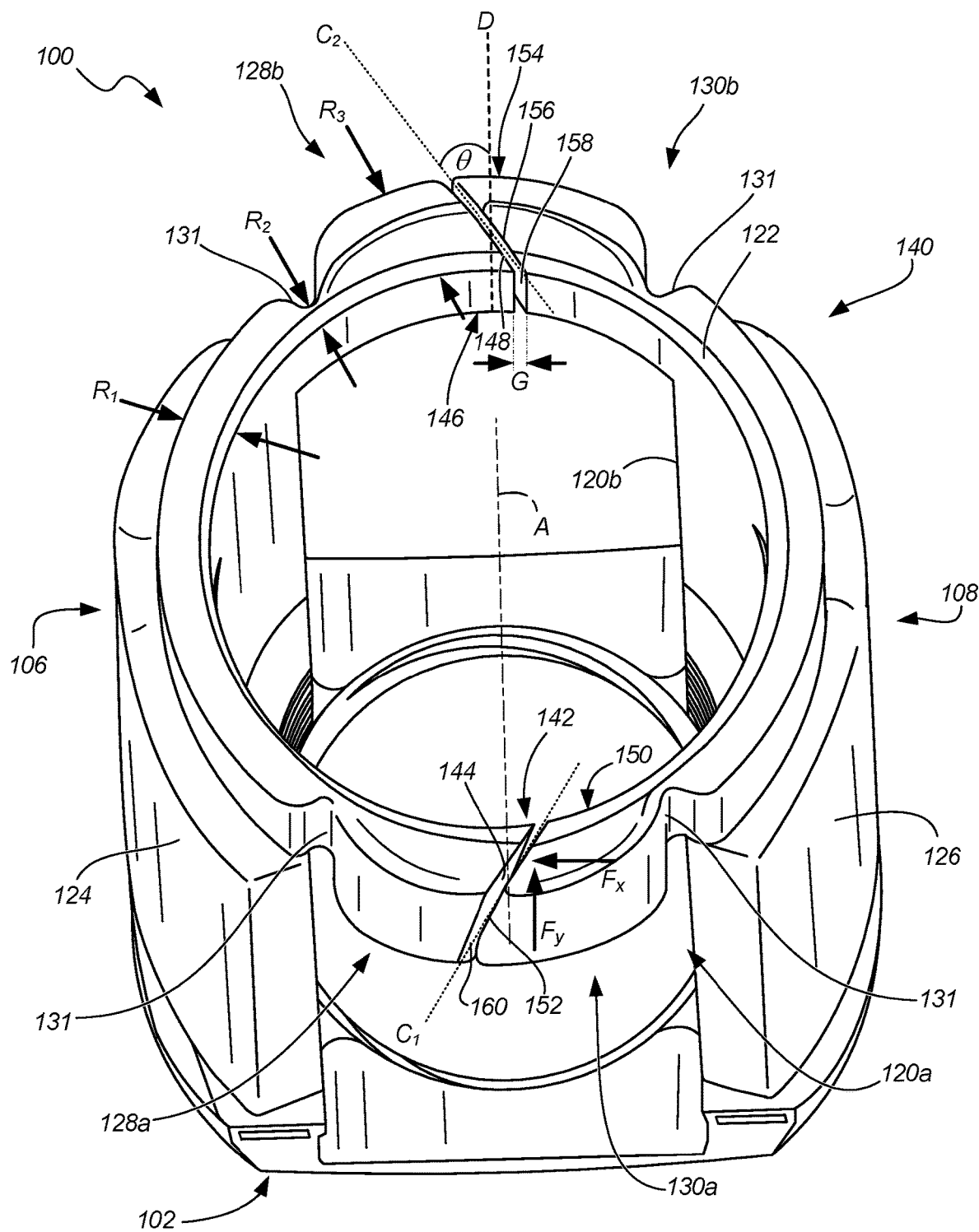
FIG. 3 illustrates an isometric view of an anchor with extended tabs from a top perspective, in accordance with at least one example of this disclosure.

FIG. 3 illustrates an isometric view of anchor 100 from a top perspective, in accordance with at least one example of this disclosure. Anchor 100 can include head 102 and extensions 106 and 108. Extensions 106 and 108 can include slots 120a and 120b, proximal opening 122, and proximal extension portion 140. Extension 106 can include elongate portion 124, and proximal supports 128a and 128b. Extension 108 can include elongate portion 126, and proximal supports 130a and 130b. Proximal support 128a can include support end 142 which can include face 144. Proximal support 128b can include support end 146 which can include face 148. Proximal support 130a can include support end 150 which can include face 152. Proximal support 130b can include support end 154 which can include face 156. Also shown in FIG. 3 are axis A, chords C1 and C2, radial thicknesses R1, R2, and R3, and forces Fx and Fy.

Anchor 100 of FIG. 3 can be consistent with FIGS. 1-2B; however, FIG. 3 shows further details of anchor 100, especially proximal supports 128a and 128b and 130a and 130b. For example, FIG. 3 shows how each proximal support includes an end having a face. Support end 142 can terminate at face 144 and support end 150 can terminate at face 152 where faces 144 and 152 can be parallel in a first condition (shown in FIG. 3) and separated by gap 160 having a distance G. Similarly, support end 146 can terminate at face 148 and support end 154 can terminate at face 156 where faces 148 and 156 can be parallel in a first condition (shown in FIG. 3) and separated by gap 158 having a distance G. In the example shown in FIG. 3, faces 144 and 152 can be substantially parallel to a first plane that is substantially parallel with chord C1 that is transverse to axis A. Faces 148 and 156 can be substantially parallel to a second plane that is substantially parallel with chord C2 that is transverse to axis A. In the example of FIG. 3, the chords C1 and C2 are not the same chord and are not parallel chords. In some examples, chords C1 and C2 can have the same angle θ relative to a diameter of axis A.

Also shown in FIG. 3 are radial thicknesses R1, R2, and R3. Radial thickness R1 can be a thickness of extension 106 proximate proximal end 140 and thickness R3 can be a thickness of proximal support 128b proximate proximal end 146 and thickness R2 can be a reduced thickness at notches 131 where each proximal support connects to each longitudinal portion (e.g., where proximal support 128b connects to longitudinal portion 124). In operation of some examples, radial thickness R2 can allow for a sleeve to slide over extended tabs 106 and 108. In some examples, radial thickness R2 can ensure that the sleeve is correctly oriented (or clocked) with respect to tabs 106 and 108, as discussed further below.

In operation of some examples, faces 144 and 152 can be separated by gap 160 and faces 148 and 156 can be separated by gap 158 in a first condition. Because extensions 106 and 108 can flex toward each other and because the proximal extensions of each extension can deflect towards each other, when forces and/or torques are applied to extensions 106 and 108, faces 144 and 152 can contact each other and/or faces 148 and 156 can contact each other to transfer forces there between. Because faces 144 and 152 are not parallel with faces 148 and 156, proximal support 128a is less likely to disengage proximal support portion 130a and proximal supports 128b is less likely to disengage proximal support portion 130b, helping to ensure forces and torques are transferrable between the proximal supports and helping to prevent extensions 106 and 108 from separating unintentionally. For example, forces transverse to axis A such as Fx and Fy can be transferred between faces 144 and 152 to allow transfer of forces between extensions 106 and 108 and therefore from head 102 to a proximal end of extensions 106 and 108. In some examples, forces may be applied to extensions 106 and/or 108 when a connecting rod is being reduced into position in head 102.

FIG. 4A illustrates an isometric front view of assembly 200, in accordance with at least one example of this disclosure. FIG. 4B illustrates an isometric side view of assembly 200, in accordance with at least one example of this disclosure. FIGS. 4A and 4B are discussed concurrently below. FIGS. 4A and 4B below discuss how sleeve 202 can be used to reinforce extended tabs 106 and 108.

Assembly 200 can include anchor 100 and sleeve 202. Anchor 100 can include head 102 and can be consistent with anchor 100 of FIGS. 1-3 above. Sleeve 202 can include arms 204 and 206, proximal portion 208, slots 210, distal end 212, and button 214.

Sleeve 202 can be a generally hollow cylindrical member including an elongate body having a central bore 216, where central bore 216 can be sized and shaped to receive anchor 100 therein. Arms 204 and 206 can extend distally from proximal portion 208 and can be separated by channels 210, which can be sized to align with channels 110 of anchor 100. Arms 204 and 206 can have a length sized to extend over extensions 106 and 108 of anchor, while exposing most of head 102. In some examples, arms 204 and 206 can have a length sized to extend over head 102.

In some examples, a distal portion of arms 204 and 206 can include an internal counterbore which can include a dovetail feature sized to allow sleeve 202 to slide over extended tabs 106 and 108 and to engage head 102 to limit axial translation and rotation of anchor 100 relative to sleeve 202. Button 214 of proximal portion 208 can be operable to secure sleeve 202 to, and release sleeve 202 from, anchor 100, as described below in FIGS. 5A-5C.

In operation of some examples, a proximal portion of anchor 100 can be inserted into distal opening 220 of sleeve 202 and can be inserted until radially inwardly extending projections of sleeve 202 engage rim interface 137 of head 102 of anchor 100. Anchor 100 can be inserted into sleeve 202 either before or after anchor 100 is inserted into a cavity and before or after anchor 100 is secured to a bone. Once anchor 100 is secured within sleeve 202, and after anchor is driven into bone, a connecting member or rod can be inserted. The connecting member can either be passed through slots 120 of anchor and passed through slots 210 of sleeve at the same time, or the connecting member can be passed through slots 120 of anchor and the sleeve 202 can be inserted over anchor 100 where the distal openings of slots 210 can receive the connected member into slots 210 of sleeve 202.

Once the rod or connecting member is reduced into place, a closure top or fastener (e.g., set screw) can be used to secure or reduce a connecting member into head 102, with sleeve 202 preventing premature breakage at 114 and 116 during this reduction. In some examples, the closure top or set screw can be used to reduce the rod through extended tabs 106 and 108. In this example, sleeve 202 can reinforce tabs 106 and 108 to help prevent premature breakage at 114 and 116 during reduction. Sleeve 202 can also be used to reinforce extended tabs 106 and 108 to prevented unwanted break off when other external forces and torques are applied to extended tabs 106 and 108. In one example, sleeve 202 can reinforce tabs 106 and 108 during hand positioning or manipulation of anchor 100, such as when rotating an anchor already secured to a vertebral body. This type of hand positioning and rotation of sleeve 202 and anchor 100 can be common during a spinal de-rotation procedure.

Figure 5A:
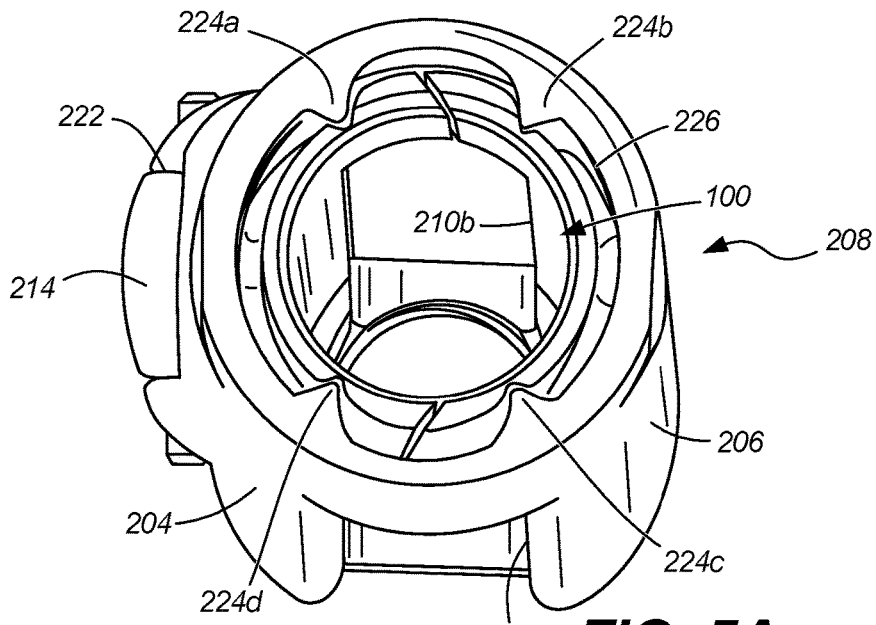
FIG. 5A illustrates an isometric top view of an anchor and sleeve assembly, in accordance with at least one example of this disclosure.
Figure 5B:
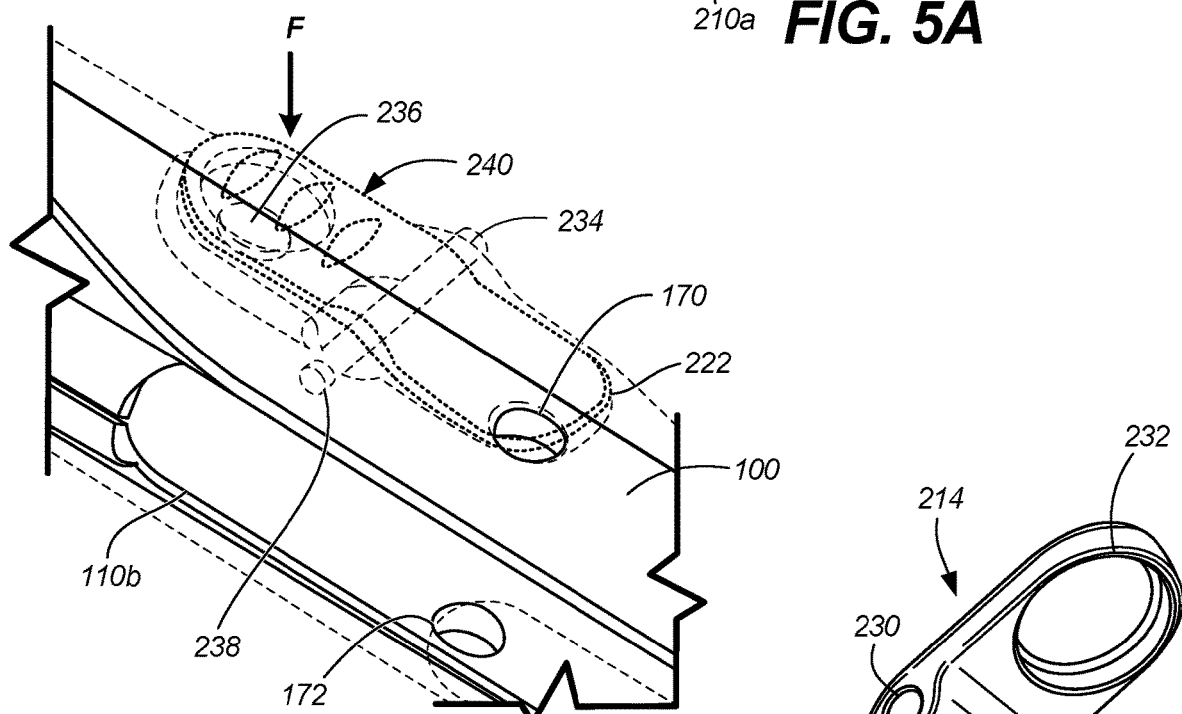
FIG. 5B illustrates an isometric side view of a portion of an anchor and sleeve assembly, in accordance with at least one example of this disclosure.
Figure 5C:
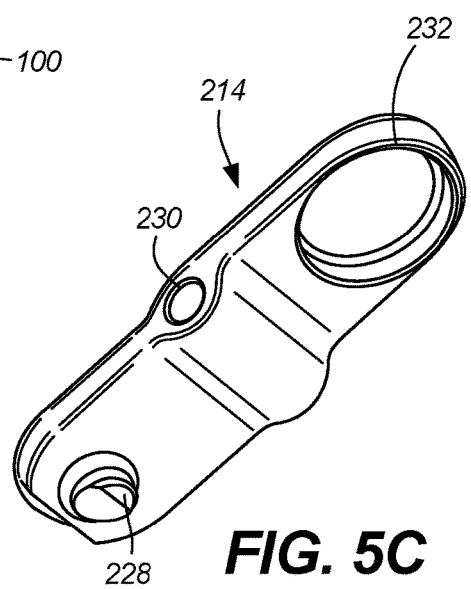
FIG. 5C illustrates an isometric bottom view of a button of an anchor and sleeve assembly, in accordance with at least one example of this disclosure.

FIG. 5A illustrates an isometric top view of assembly 200, in accordance with at least one example of this disclosure. FIG. 5B illustrates an isometric side view of a portion of assembly 200, in accordance with at least one example of this disclosure. FIG. 5C illustrates an isometric bottom view of button 214 of assembly 200, in accordance with at least one example of this disclosure. FIGS. 5A-5C are discussed concurrently below.

Assembly 200 and anchor 100 shown in FIGS. 5A-5C can be consistent with FIGS. 1-4B discussed above; however, FIGS. 5A-5C show additional details of assembly 200 and especially of sleeve 202. For example, FIG. 5A shows projections 224a-224d that can extend radially inward from bore 226 of sleeve 202 and can extend from a proximal end of proximal portion 208 to or near a distal portion of sleeve 202. In operation, projections 224a-224d can each interface with one of notches 131 (shown in FIG. 3) allowing sleeve 202 to interlock with extended tabs 106 and 108 of anchor 100, helping to limit rotation of sleeve 202 relative to anchor 100. Though four of projections 224a-224d are shown, more or less can be used. For example, 1, 2, 3, 5, 6, 7, 8, and the like projections can be used. Though projections 224a-224d are shown to have a generally triangular shape, other shapes can be used.

FIG. 5A also shows how button 214 is insertable into button recess 222 of sleeve 202. This can allow button 214 to engage anchor 100 (as discussed below) and can reduce an amount button 214 extends beyond an outer radial surface of sleeve 202. This can help to reduce button 214 from catching on instruments and other objects during a procedure.

FIGS. 5B and 5C show button 214 and how button 214 interacts with anchor 100. For example, FIG. 5C shows button projection 228, which can be a protuberance extending from a bottom surface of button 214. FIG. 5C also shows recess 232 which can be a cavity or recess into a bottom surface of button 214. In some examples, recess 232 can be sized to retain a spring and can also be sized to receive boss 236 of sleeve 202, such that boss 236 of sleeve 202 can extend into recess 232 when force F is applied to button 214. Recess 232 can limit movement of a spring relative to boss 236 and therefore sleeve 202. FIG. 5C also shows button bore 230, which can be sized to receive pin 234 therethrough.

FIG. 5B shows how button 214 interacts with sleeve 202. For example, button 214 is disposable within button recess 222 such that button bore 230 aligns with pin bore 238 of sleeve 202 allowing pin 234 to extend through button bore 230 and pin bore 238 so that button 214 can pivot within recess 222 about pin 234. In some examples, button projection 228 can extend into one of projection bores 170 and 172 in a first position, as shown in FIG. 5B.

Button 214 can be biased to pivot to the first position by one or more biasing elements, such as a spring, so that projection 228 of button 214 engages projection bore 170 to limit axial movement of anchor 100 relative to sleeve 202. Then, when it is desired to remove sleeve 202 from anchor 100, force F can be applied to proximal portion 240 of button 214 to pivot button 214 about pin 234, removing projection 228 from projection bore 170 and allowing sleeve 202 to move axially such that sleeve 202 can be removed from anchor 100.

Figure 6:
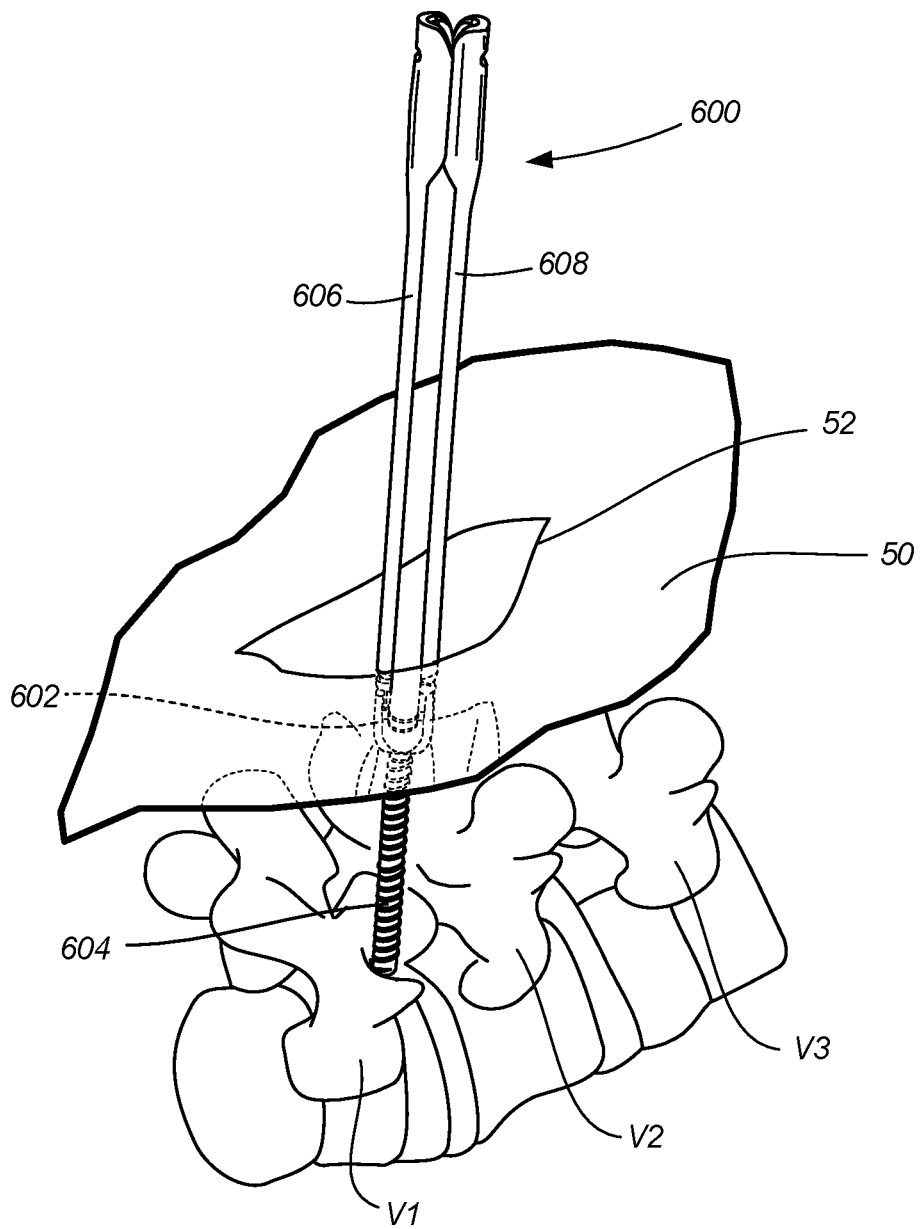
FIG. 6 illustrates an isometric view of an anchor with extended tabs, in accordance with at least one example of this disclosure.

FIG. 6 illustrates an isometric view of anchor 600, in accordance with at least one example of this disclosure. Anchor 600 can include head 602, shank 604, first extension 606, and second extension 608. Also shown in FIG. 6 are cutaneous portion 50, opening 52, and vertebrae V1, V2, and V3.

Anchor 600 of FIG. 6 can be consistent with anchor 100 discussed above, apart from the differences discussed below with respect to FIG. 7. Also, FIG. 6 shows how anchor 600 can be used in an example operation. In operation of some examples, an incision can be made on a posterior portion of a patient along the patient's vertebral column, for example, along the patient's thoracic spine. For example, an incision can be made on cutaneous portion 50 where the incision extends through the dermis and subcutaneous tissue to create opening 52 and exposes or partially exposes vertebrae V1-V3. In some cases, multiple incisions can be made to minimize invasion. Next, a punch may be used to break the cortical bone to create a pilot or guide hole in a vertebra for anchor 600. Once the vertebra (for example, vertebra V1) is prepared, anchor 600 can be extended into opening 52 such that anchor 600 can be engaged with vertebra V1, for example. Shank 604 of anchor 600 can then be driven into, for example, a pedicle of vertebra V1 to secure anchor 600 to vertebra V1 while extensions 606 and 608 can extend beyond opening 52.

While in this position, extensions 606 and 608 can receive a support instrument thereon and extensions 606 and 608 and/or the instrument can be manipulated by hand to position vertebra V1, such as during a de-rotation procedure. During this rotation, the instrument and proximal supports can help prevent unwanted separation of extensions 606 and 608.

Figure 7:
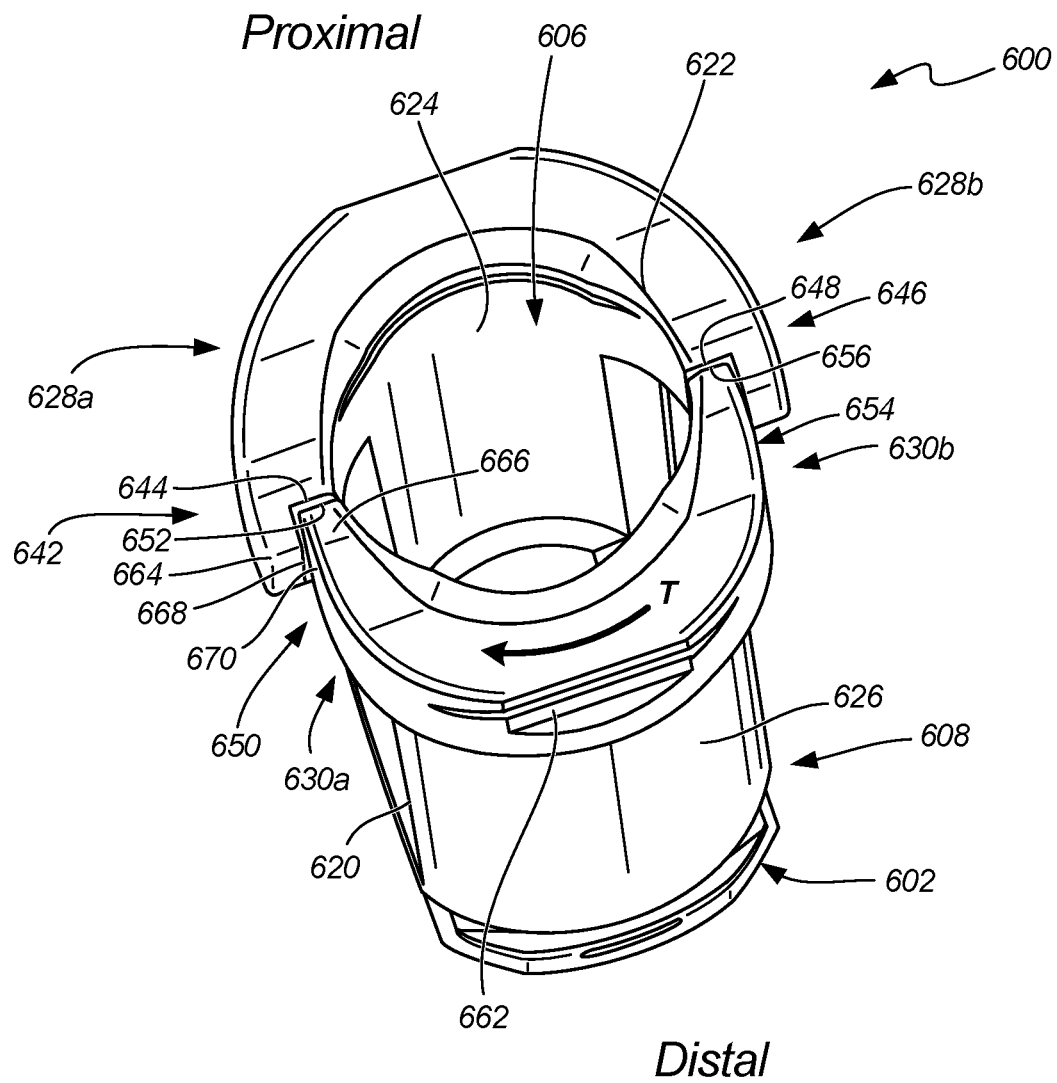
FIG. 7 illustrates an isometric top view of an anchor with extended tabs, in accordance with at least one example of this disclosure.

FIG. 7 illustrates an isometric top view of anchor 600, in accordance with at least one example of this disclosure. Anchor 600 can include head 602, first extension 606 and second extension 608. First extension 606 can include elongate portion 624 and proximal supports 628a and 628b. Second extension 608 can include elongate portion 626 and proximal supports 630a and 630b. First extension 606 and second extension 608 can include slots 620 and proximal opening 622. Proximal support 628a can include support end 642 which can include face 644. Proximal support 628b can include support end 646 which can include face 648. Proximal support 630a can include support end 650 which can include face 652. Proximal support 630b can include support end 654 which can include face 656. Each of first extension 606 and second extension 608 can include notch 662. Proximal support 628a can also include overlapping portion 664 and inner face 668. Proximal support 630a can also include nesting portion 666 and outer face 670. Also shown in FIG. 7 are orientation indicators Proximal and Distal.

Anchor 600 can be consistent with anchor 100 discussed above with respect to FIGS. 1-5C, except that a proximal portion of anchor 600 can be different. For example, notch 662 of each of first extension 606 and second extension 608 can be a undercut or recess in an outer surface of each of extension 606 and second extension 608 proximate a proximal termination of each of extension 606 and second extension 608. In some examples, notch 662 can be sized and configured to engage with other tools (such as a driver) in other examples.

Anchor 600 also differs from anchor 100 in that it can include overlapping proximal supports. That is, proximal supports 628a and 628b can substantially form a c-shape from a top or proximal perspective and proximal supports 630a and 630b substantially form a c-shape from a top or proximal perspective, where proximal supports 630a and 630b can nest within proximal supports 628a and 628b.

For example, proximal support 628a can include an undercut and overlapping portion 664, which can extend circumferentially beyond face 644. The undercut or notch can be defined by face 644 (which can be radially extending) and face 668 (which can be circumferentially extending). Nesting portion 666 of proximal support 630a can include face 652 which can be a radially extending face engageable with face 644. Nesting portion 666 can also include face 670 which can be a circumferentially extending and radially outer face of nesting portion 666 that can interface with face 668. In operation, when nesting portion 666 is nested within the undercut of proximal support 628a, forces and torques (such as those produced by torque T) can be transferred between face 644 and face 652 and between face 668 and 670. Also, the nesting of proximal supports 630a and 630b can help reduce unwanted separation of extensions 606 and 608 from head 602.

Figure 8:
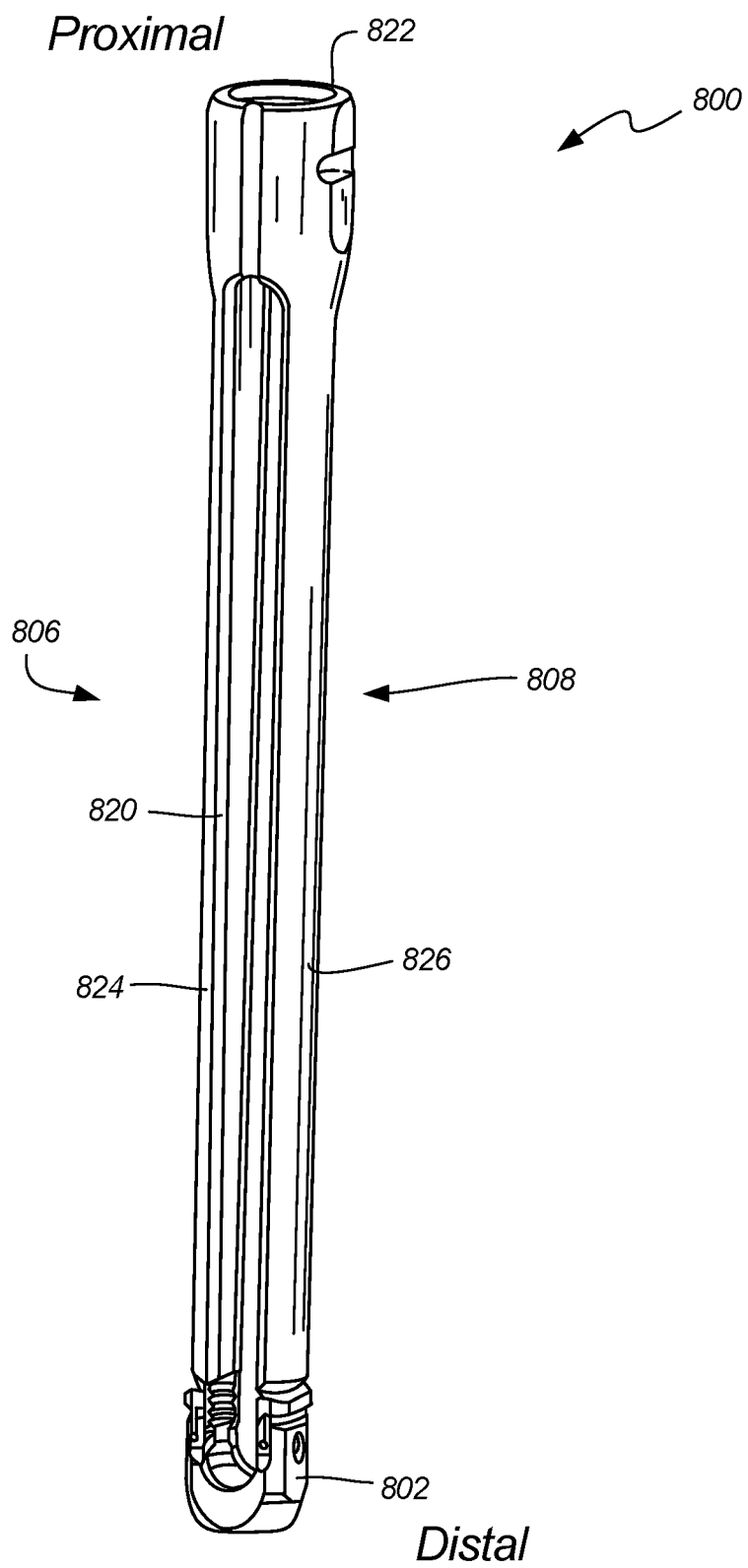
FIG. 8 illustrates an isometric front view of an anchor with extended tabs, in accordance with at least one example of this disclosure.
Figure 9:
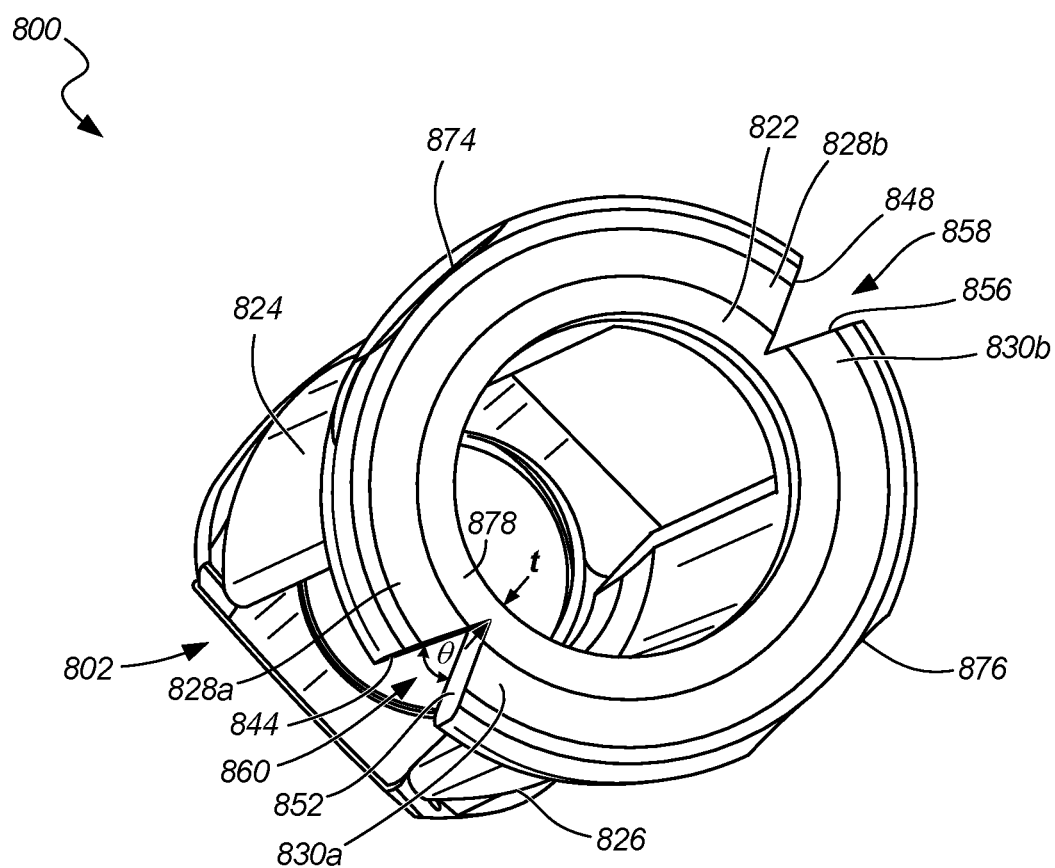
FIG. 9 illustrates an isometric top view of an anchor with extended tabs, in accordance with at least one example of this disclosure.

FIG. 8 illustrates an isometric front view of anchor 800, in accordance with at least one example of this disclosure. FIG. 9 illustrates an isometric top view of anchor 800, in accordance with at least one example of this disclosure. FIGS. 8 and 9 are discussed below concurrently.

Anchor 800 can include head 802, first extension 806 and second extension 808. First extension 806 can include elongate portion 824 and second extension 808 can include elongate portions 826, where elongate portions 824 and 826 can define slots 820 there between. First extension 806 can also include proximal supports 828a and 828b and second extension 808 can include proximal supports 830a and 830b, which can define proximal opening 822. Proximal support 828a can include face 844 and proximal support 830a can include face 852 where faces 844 and 852 together form notch 860. Similarly, proximal support 828b can include face 848 and proximal support 830b can include face 856 where faces 848 and 856 together form notch 858.

Each of notches 858 and 860 can be located at a junction between proximal supports. For example, notch 858 can be formed by a meeting of faces 848 and 856 such that bridge 878 remains, connecting proximal supports 828a and 830a, where bridge 878 can have a thickness t. Notch 860 can similarly connect proximal supports 828b and 830b.

In operation of some examples, torque T can be transferrable between proximal supports 828a and 830a through bridge 878 to allow a torque to be transferred from a proximal end of anchor 800 to a distal end (head 802) to drive a shank into a bone. Torque T can be similarly transferred between proximal supports 828b and 830b. In some examples, bridge 878 can allow torque T (and forces) to be transferred between proximal supports while helping to prevent unwanted breakaway of extensions 806 and 808 from head 802.

Notch 860 can have an acute angle in some examples, and an obtuse angle in other examples. The angle θ, of notch 860 can be selected based on a desired amount of force required to separate proximal supports 828 from proximal supports 830. In some examples, proximal supports 828 from proximal supports 830 can be formed of one piece to create notches 858 and 860, such as through machining processes.

First extension 806 can also include interface portion 874 and second extension 808 can also include interface portion 876. Each of interface portions 874 and 876 can be a flat portion or face in an outer surface of each of extension 806 and second extension 808, respectively, proximate a proximal termination of each of extension 806 and second extension 808. In some examples, each of interface portions 874 and 876 can be sized and configured to engage with a support instrument in some examples, and can be configured to engage with other tools (such as a driver) in other examples.

Figure 10:
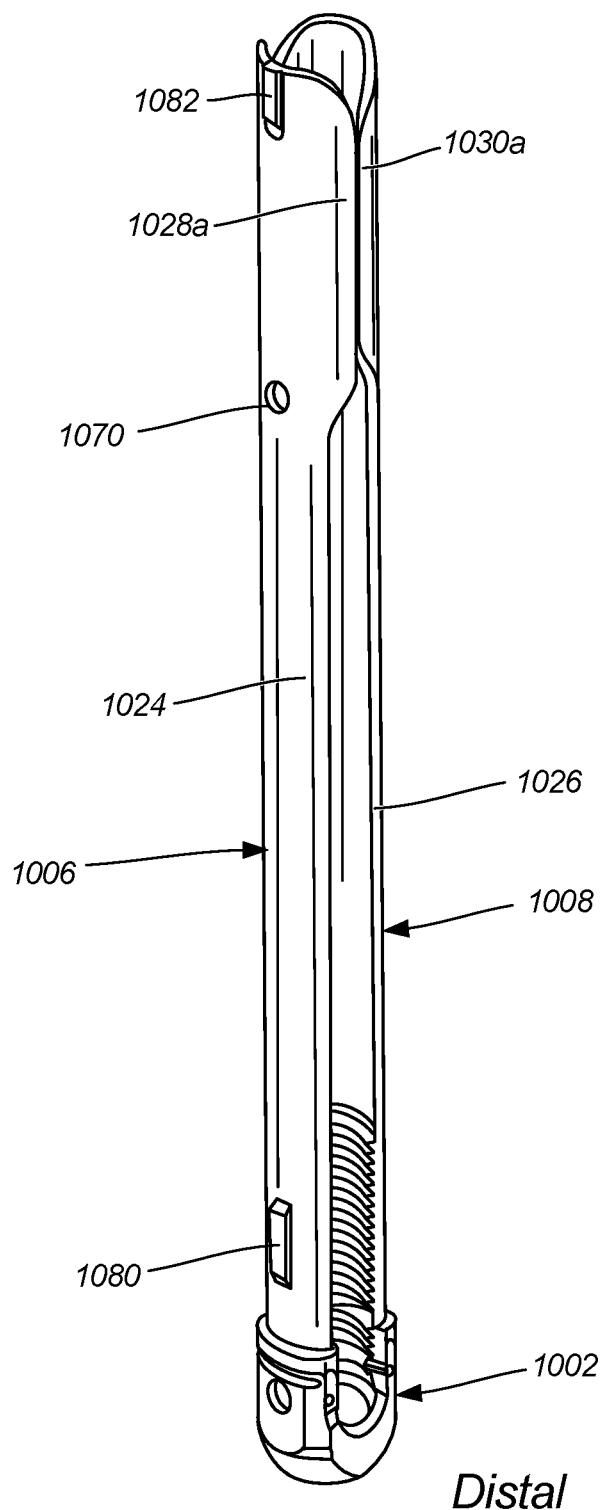
FIG. 10 illustrates an isometric front view of an anchor with extended tabs, in accordance with at least one example of this disclosure.
Figure 11:
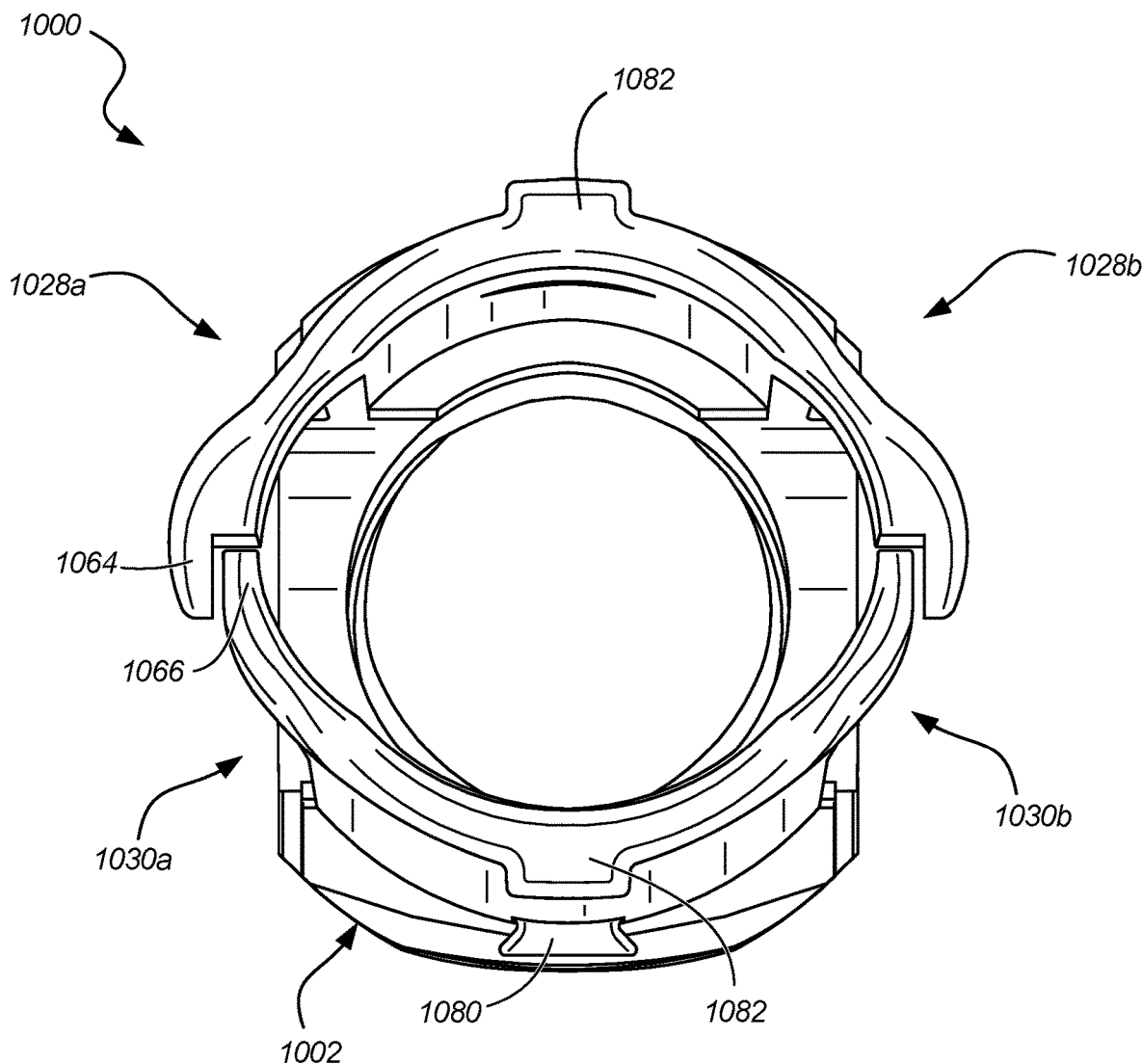
FIG. 11 illustrates an isometric top view of an anchor with extended tabs, in accordance with at least one example of this disclosure.

FIG. 10 illustrates an isometric front view of anchor 1000, in accordance with at least one example of this disclosure. FIG. 11 illustrates an isometric top view of anchor 1000, in accordance with at least one example of this disclosure. FIGS. 10 and 11 are discussed below concurrently.

Anchor 1000 can include head 1002, first extension 1006, and second extension 1008. First extension 1006 can include elongate portion 1024, proximal supports 1028a and 1028b, projection bore 1070, distal projection 1080, and proximal projection 1082. Second extension 1008 can include elongate portion 1026, proximal supports 1030a and 1030b, projection bore 1070, distal projection 1080, and proximal projection 1082.

Anchor 1000 can be similar to anchor 600 in that proximal supports 1028a and 1028b can have a geometric shape that is substantially a c-shape and proximal supports 1030a and 1030b can have a geometric shape that is substantially a c-shape that nests within proximal supports 1028a and 1028b. For example, nesting portion 1066 of proximal support 1030a can nest within proximal support 1028a such that overlapping portion 1064 overlaps nesting portion 1066.

Anchor 1000 can differ from anchor 600 in that anchor 1000 includes distal projections 1080 and proximal projections 1082. Proximal projections 1082 can extend radially from outer surfaces of elongate portions 1024 and 1026. Each of proximal projection 1082 can have a substantially rectangular prismatic shape that is axially extending and can be configured to interact with a channel of a sleeve, in some examples.

Similarly, distal projections 1080 can extend radially from outer surfaces of elongate portions 1024 and 1026. Each of distal projections 1082 can substantially form an axially extending tail configured to engage a socket of a sleeve (similar to sleeve 202 of FIGS. 4A-5C) similar to a dovetail engagement, and can be configured to engage with other tools (such as a driver) in other examples.

Figure 12A:
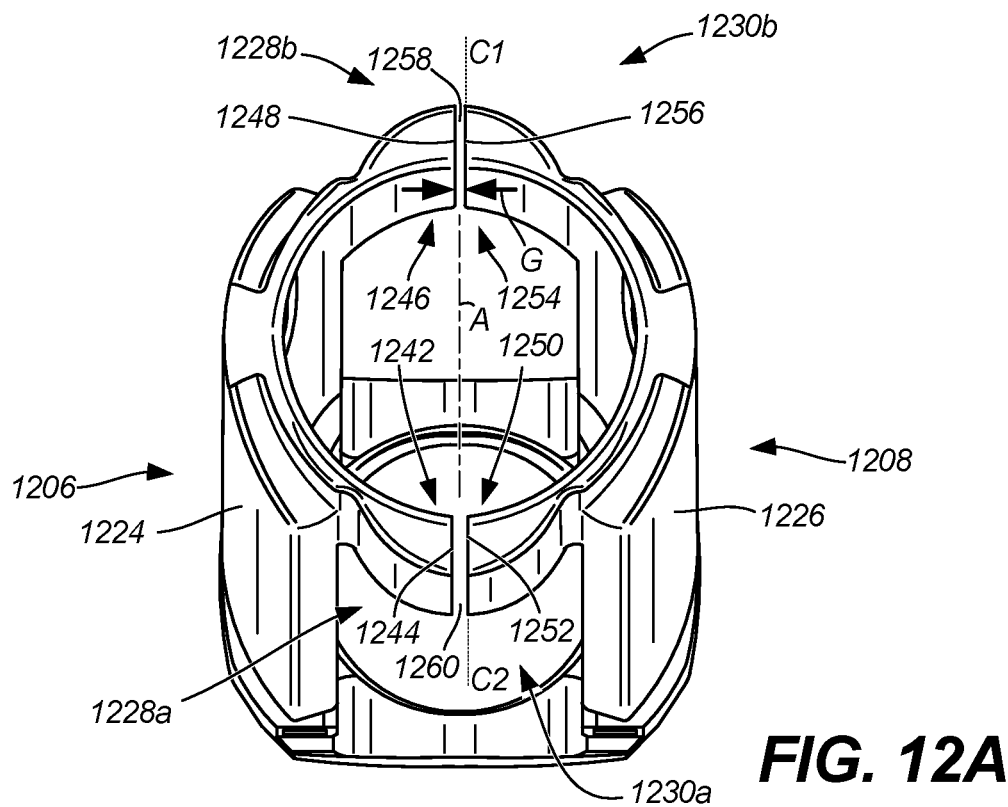
FIG. 12A illustrates an isometric top view of an anchor with extended tabs in a first condition, in accordance with at least one example of this disclosure.
Figure 12B:
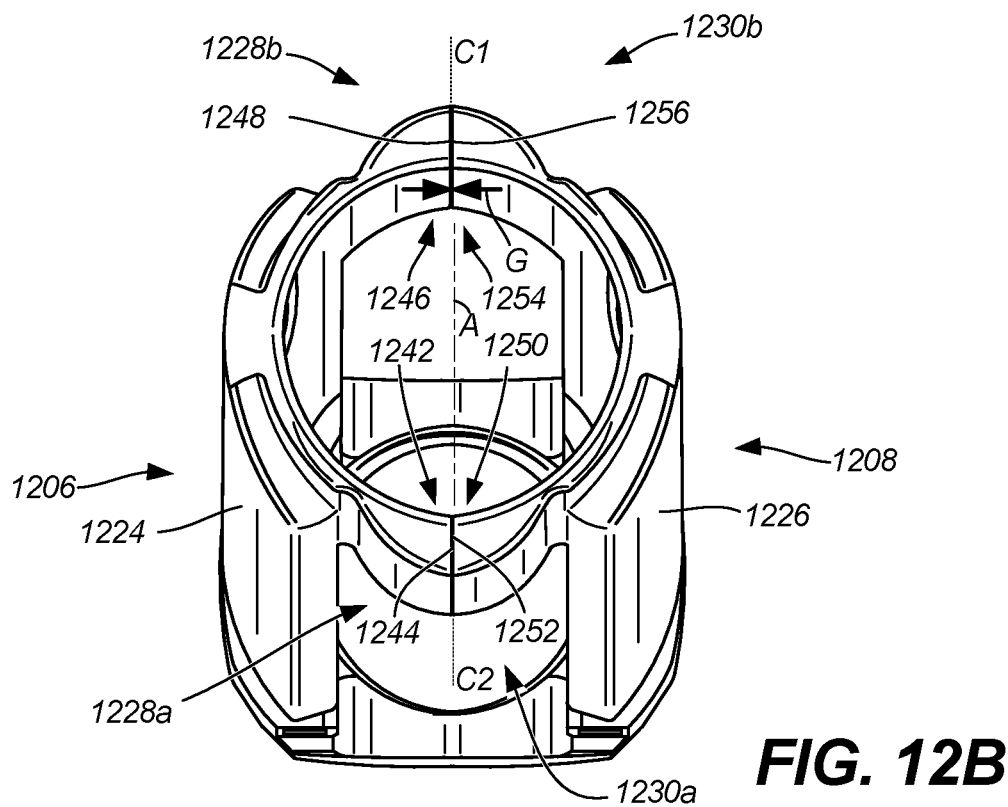
FIG. 12B illustrates an isometric top view of an anchor with extended tabs in a second condition, in accordance with at least one example of this disclosure.

FIG. 12A illustrates an isometric top view of anchor 1200 in a first condition, in accordance with at least one example of this disclosure. FIG. 12B illustrates an isometric top view of anchor 1200 in a second condition, in accordance with at least one example of this disclosure. FIGS. 12A and 12B are discussed below concurrently.

Anchor 1200 can include head 1202 and extensions 1206 and 1208. Extension 1206 can include elongate portion 1224, and proximal supports 1228a and 1228b. Extension 1208 can include elongate portion 1226, and proximal supports 1230a and 1230b. Proximal support 1228a can include support end 1242 which can include face 1244. Proximal support 1228b can include support end 1246 which can include face 1248. Proximal support 1230a can include support end 1250 which can include face 1252. Proximal support 1230b can include support end 1254 which can include face 1256. Also shown in FIG. 12 are axis A and chords C1 and C2.

Anchor 1200 of FIG. 12 can be similar to anchor 300 of FIG. 3 with differing proximal supports. Support end 1242 can terminate at face 1244 and support end 1250 can terminate at face 1252 where faces 1244 and 1252 can be parallel in a first condition (shown in FIG. 12A) and separated by gap 1260 having a distance G. Similarly, support end 1246 can terminate at face 1248 and support end 1254 can terminate at face 1256 where faces 1248 and 1256 can be parallel in a first condition (shown in FIG. 12A) and separated by gap 1258 having a distance G.

In the example shown in FIG. 12A, faces 1244 and 1252 can be substantially parallel to a first plane that is substantially parallel with chord C1 that is transverse to axis A and faces 1248 and 1256 can be substantially parallel to a second plane that is substantially parallel with chord C2 that is transverse to axis A. In the example of FIG. 12A, the chords C1 and C2 can be parallel (and can be the same chord).

In operation of some examples, faces 1244 and 1252 can be separated by gap 1260 and faces 1248 and 1256 can be separated by gap 1258 in a first condition (shown in FIG. 12A). Because extensions 1206 and 1208 can flex toward each other and because the proximal extensions can deflect towards each other, when forces and/or torques are applied to extensions 1206 and 1208, faces 1244 and 1252 can contact each other and/or faces 1248 and 1256 can contact each other (shown in FIG. 12B) to transfer forces there between where gap G is eliminated.

Figure 13A:
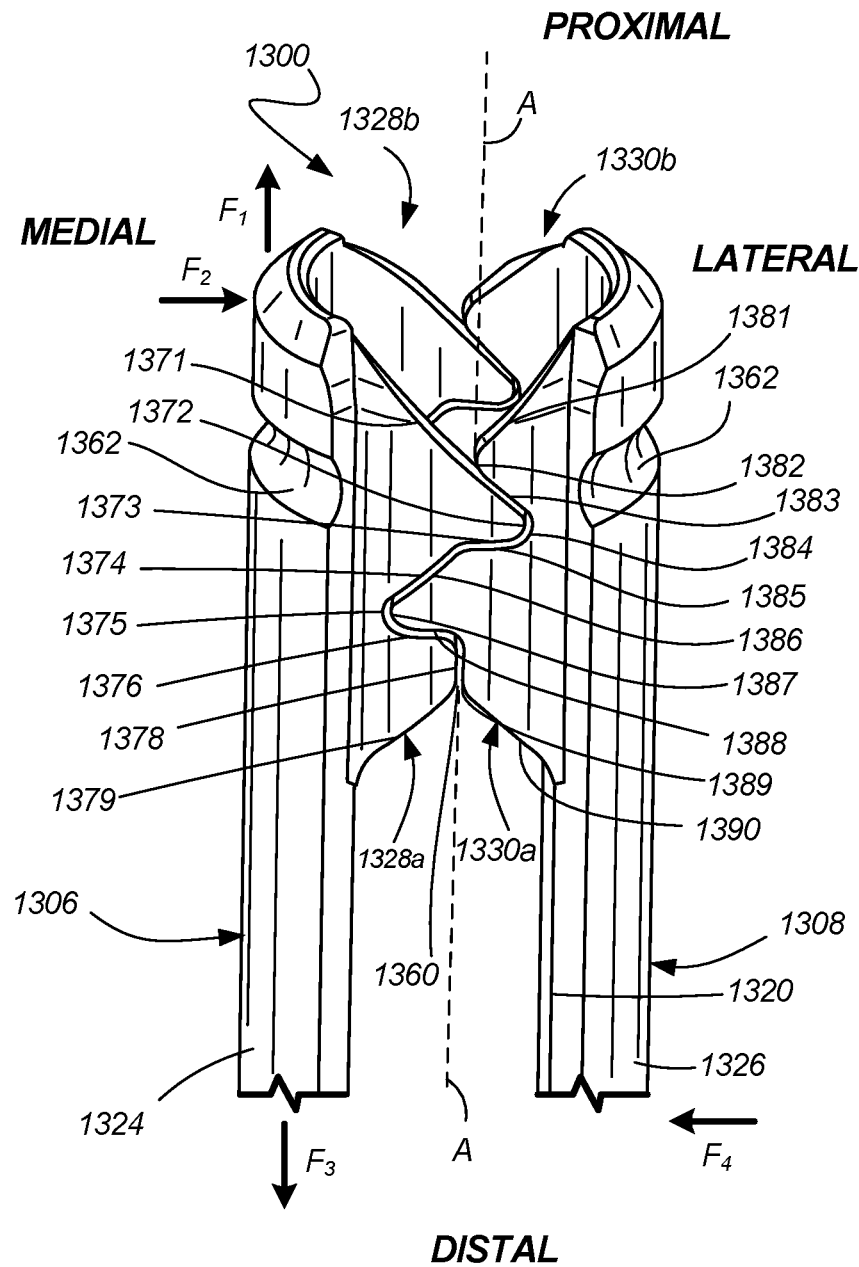
FIG. 13A illustrates an isometric front view of an anchor with extended tabs, in accordance with at least one example of this disclosure.
Figure 13B:
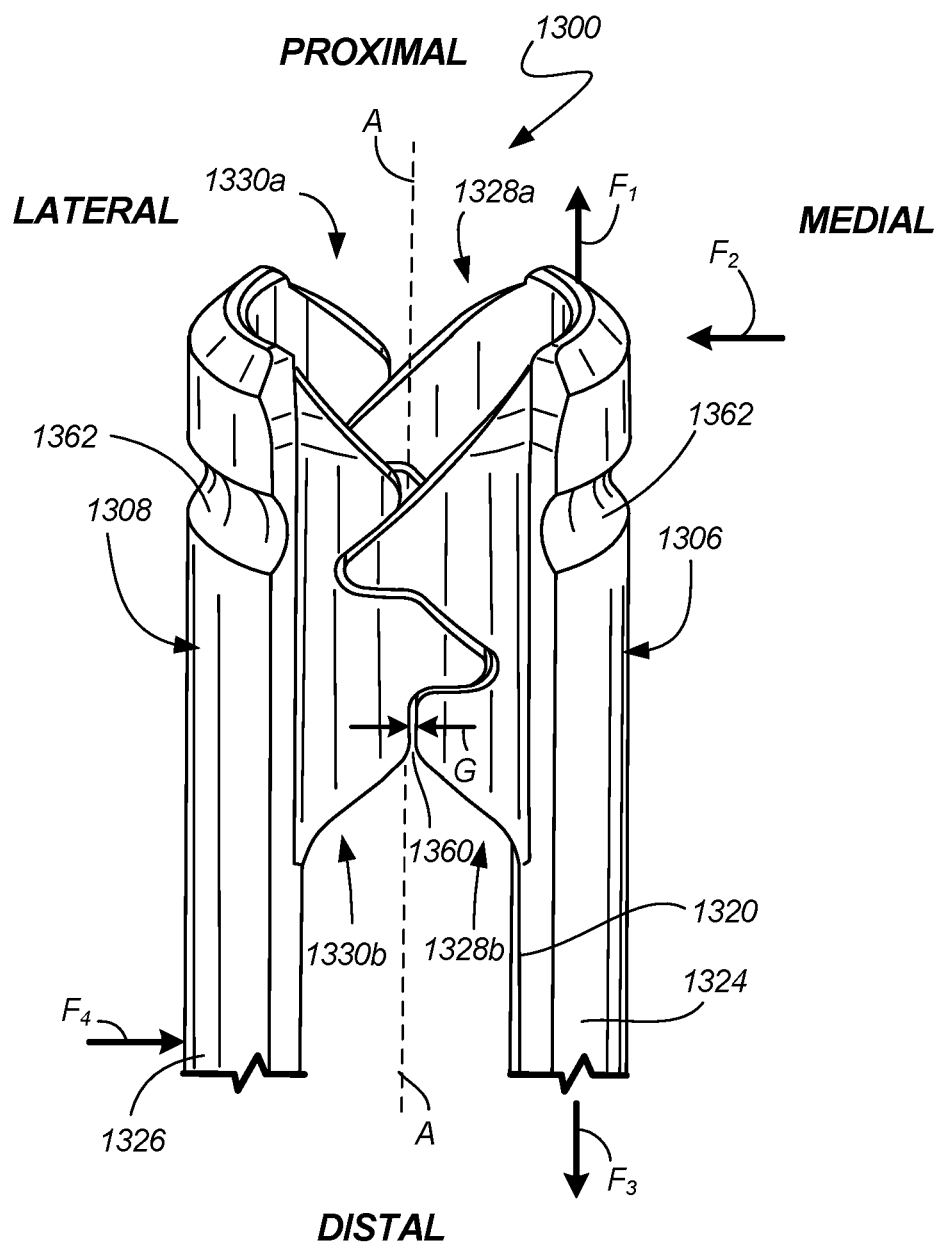
FIG. 13B illustrates an isometric back view of an anchor with extended tabs, in accordance with at least one example of this disclosure.

FIG. 13A illustrates an isometric front view of anchor 1300 with extended tabs, in accordance with at least one example of this disclosure. FIG. 13B illustrates an isometric back view of anchor 1300 with extended tabs, in accordance with at least one example of this disclosure. Anchor 1300 can include interlocking proximal supports, where medial and lateral tabs can interlock without connecting and can connect to each other in response to forces to help limit relative movement of extended tabs to help reduce accidental breakoff of the extensions from the anchor head. Many of the previously discussed anchors can be modified to include interlocking proximal supports. Anchor 1300 is discussed further below with respect to FIGS. 13A and 13B. Note, the following discussion utilizes terms such as proximal, distal, medial, and lateral as relative directional references to assist the reader with understanding the structure of the device. The device does not necessarily have to be utilized with the various structures aligned with a patient in accordance with these directions.

Anchor 1300 can include a head and extensions 1306 and 1308. Extension 1306 can include elongate portion 1324 and proximal supports 1328a and 1328b. Extension 1308 can include elongate portion 1326 and proximal supports 1330a and 1330b. Extensions 1306 and 1308 can be separated, distal of proximal supports 1328 and 1330, by channels 1320, and can also include groove 1362. Each of proximal supports 1328a and 1328b can include proximal ramp 1371, proximal tongue 1372, proximal flat 1373, medial ramp 1374, distal groove 1375, distal flat 1376, vertical face 1378, and distal ramp 1379. Each of proximal supports 1330a and 1330b can include first proximal ramp 1381, proximal tongue 1382, second proximal ramp 1383, proximal groove 1384, proximal flat 1385, medial ramp 1386, distal tongue 1387, distal flat 1388, vertical face 1389, and distal ramp 1390. Also shown in FIGS. 13A and 13B are axis A, forces F1, F2, F3, and F4, distance G, and orientation indicators Proximal, Distal, Medial, and Lateral.

Groove 1362 can be a circumferential groove extending around substantially all of an outer portion of extensions 1306 and 1308, but can be separated by proximal supports 1328 and 1330. In some examples, groove 1362 can be sized and shaped to receive a projection therein, such as one or more balls. The projection can engage the groove to retain extensions 1306 and 1308, such as within a sleeve or reinforcement tool.

Each of proximal supports 1328*a* and 1330*a* can terminate at opposing faces defined by the various projections and grooves, discussed in detail further below. Each of the faces of portions of proximal supports 1328*a* and 1330*a* can be parallel and separated by gap 1360 having distance G in a first condition (shown in FIG. 13B). Proximal supports 1328*b* and 1330*b* can be similarly configured. Proximal supports 1328*a* and 1328*b* can include a geometry configured to engage proximal supports 1330*a* and 1330*b*, respectively, in response to forces (such as F1, F2, and F3) to help limit unwanted or accidental separation of extensions 1306 and 1308 from a head (such as head 102) of anchor 1300. Each of the proximal supports 1328 and 1330 extend radially inward from proximal sections of extensions 1306 and 1308 to engage opposing proximal supports along gap 1360.

The portions of proximal support 1328*a* can be connected as follows, proximal ramp 1371 can extend distally and laterally from a proximal termination of proximal support 1328*a* where proximal ramp 1371 can transition into proximal tongue 1372. Proximal tongue 1372 can be a laterally extending protrusion or extension from proximal ramp 1371 including a rounded termination, tongue, or nose that connects or transitions to proximal flat 1373. Proximal flat 1373 can be a substantially horizontal (with respect to an orientation of FIGS. 13A and 13B) portion or segment of proximal support 1328*a* extending medially from proximal tongue 1372 and connecting to medial ramp 1374. Medial ramp 1374 can extend medially and distally from proximal flat 1373. In one example, medial ramp 1374 can be substantially orthogonal, though not directly connected, to proximal ramp 1371. Medial ramp 1374 can connect to distal groove 1375 which can be a groove or recess extending medially and including a curved profile configured to connect medial ramp 1374 to distal flat 1376, which can be a substantially horizontal portion extending laterally from distal groove 1375. Distal flat 1376 can be connected by a rounded corner to vertical face 1378, which can extend substantially distally from vertical face 1378 before connecting to distal ramp 1379, which can extend distally and medially from vertical face 1378. The same portions of proximal support 1328*b* can be connected similarly. Further, each of proximal ramp 1371, proximal tongue 1372, proximal flat 1373, medial ramp 1374, distal groove 1375, distal flat 1376, vertical face 1378, and distal ramp 1379 can be connected by one or more transitions, such as corners or turns that can include a rounded or radiused profile.

The portions of proximal support 1330*a* can be connected as follows, first proximal ramp 1381 can extend distally and medially from a proximal termination of proximal support 1330*a* where first proximal ramp 1381 can transition into proximal tongue 1382. Proximal tongue 1382 can be a medially extending protrusion or extension from first proximal ramp 1381 including a rounded termination, tongue, or nose that connects or transitions to second proximal ramp 1383. Second proximal ramp 1383 can extend laterally and distally from proximal tongue 1382 substantially orthogonally to first proximal ramp 1381 (in some examples) and can connect to proximal groove 1384. Proximal groove 1384 can be a groove or recess extending laterally and including a curved profile configured to connect second proximal ramp 1383 to proximal flat 1385. Proximal flat 1385 can be a substantially horizontal portion or segment of proximal support 1330*a* extending laterally from proximal groove 1384 and connecting to medial ramp 1386. Medial ramp 1386 can extend substantially medially and distally from proximal flat 1385. In one example, medial ramp 1386 can be substantially parallel to proximal ramp 1381 and substantially orthogonal to second proximal ramp 1382. Distal tongue 1387 can connect to medial ramp 1386 and can extend substantially medially therefrom. Distal tongue 1387 can be a rounded termination, tongue, or nose that connects or transitions to distal flat 1388, which can extend substantially horizontally laterally from distal tongue 1387 and can connect to vertical face 1389. Distal flat 1388 be connected by a rounded corner to vertical face 1389, which can extend substantially vertically distally from distal tongue 1388. Vertical face 1389 can connect to distal ramp 1390, which can extend laterally and distally therefrom and can be substantially parallel to second proximal ramp 1383. The same portions of proximal support 1330*b* can be connected similarly. Further, each of first proximal ramp 1381, proximal tongue 1382, second proximal ramp 1383, proximal groove 1384, proximal flat 1385, medial ramp 1386, distal tongue 1387, distal flat 1388, vertical face 1389, and distal ramp 1390 can be connected by one or more transitions, such as corners or turns that can include a rounded edge and/or radiused profile.

The engagement and interaction between proximal supports 1328*a* and 1330*a* are described with reference to operation of some examples below. Proximal ramp 1371 and proximal ramp 1381 can converge together as they extend distally to substantially form a V-shape from a front view with respect to FIGS. 13A and 13B. This configuration can allow proximal ramp 1371 and proximal ramp 1381 to operate as lead-ins for a connection member or rod and/or an insertion tool. That is, a connection member, which can have a cylindrical cross-section, can be oriented with an axis of the connection member substantially orthogonally to axis A and can be inserted through proximal supports 1328*a* and 1330*a* (and proximal supports 1328*b* and 1330*b*) by being forced (in a direction substantially parallel to axis A) into proximal ramp 1371 and proximal ramp 1381. This engagement of the connection member with proximal ramp 1371 and proximal ramp 1381 can force extension 1306 to move medially and extension 1308 to move laterally as proximal supports 1328*a* and 1330*a* separate to allow the connection member to be woven proximally to distally through proximal supports 1328*a* and 1330*a*, with proximal supports 1328*a* and 1330*a* (and proximal supports 1328*b* and 1330*b*) acting as guides. Further, second proximal ramp 1383 and medial ramps 1374 and 1386 can further guide the connection member distally as it is passed between proximal supports 1328*a* and 1330*a* and into channel 1320 for further insertion into a head of anchor 1300.

As noted above, each transition between portion of proximal supports 1328*a* and 1330*a* can be rounded and/or smooth, which can help reduce catching of the connection member on the various portions of proximal supports 1328*a* and 1330*a* (and the portions therebetween) while the connection member is being moved between proximal supports 1328*a* and 1330*a* (and proximal supports 1328*b* and 1330*b*) to channel 1320. For example, proximal tongues 1371 and 1382 and distal tongue 1387 can be rounded to help reduce friction (and catching) of the connection member as it passes between the tongues and grooves.

The components of proximal supports 1328*a* and 1330*a* can provide additional functionality. For example, during manipulation of anchor 1300 (for example, during a spinal de-rotation procedure), various forces can be applied to anchor 1300. In some examples, a tensile force can be applied to one extension, such as force F1 applied to extension 1306 (as shown in FIG. 13B). Because the tensile force may be asymmetrically applied to extensions 1306 and 1308 (that is a tensile force applied to extension 1306 may be greater than that applied to extension 1308), force F1 can cause movement, such as axial translation, of extension 1306 relative to extension 1308.

In some cases, this translation can cause premature or undesired separation of extension 1306 from a head of anchor 1300. However, here, contact between proximal supports 1328a and 1330a and between proximal supports 1328b and 1330b can distribute the force to help limit break off. More specifically, when extension 1306 translates in a proximal direction (direction of force F1), distal flat 1376 of proximal supports 1328a and 1328b can contact distal flat 1388 of proximal supports 1330a and 1330b, respectively, to transfer a portion of force F1 (in some examples approximately half of the force) to extension 1308. Further, engagement between other complimentary portions of proximal supports 1328a and 1328b and proximal supports 1330a and 1330b can further help to transfer force between extensions 1306 and 1308. For example, force transfer can occur between proximal ramp 1371 and second proximal ramp 1383. These load transfers can help to prevent breakoff of extension 1306 due to force F1 or other tensile forces.

Similarly, a force in the direction of F1 (of a proximal direction) applied to extension 1308 can be transferred to extension 1306 by contact between proximal flat 1373 and proximal flat 1385. Further, engagement between other complimentary portions of proximal supports 1328a and 1328b and proximal supports 1330a and 1330b can further help to transfer force between extensions 1306 and 1308. For example, force transfer can occur between medial ramp 1374 and medial ramp 1386. These load transfers can help to prevent breakoff of extension 1308 due to a force similar to force F1 applied to extension 1308. Also, force F2 applied to extension 1306 can cause a similar interaction.

In some examples, a force substantially or partially orthogonal to axis A can be applied to one or more extensions 1306 and 1308. For example, force F2 can be applied to extension 1306. In this example, the complimentary surfaces of proximal supports 1328a and 1328b and proximal supports 1330a and 1330b can contact each other to help limit pinching in. Specifically, vertical face 1378 and vertical face 1389 can contact each other to transfer loads therebetween to limit pinching in and to limit bending of one extension (such as extension 1306) relative to the other (such as extension 1308). Similarly, force F4 can be transferred between extensions 1306 and 1308 through complimentary surfaces of proximal supports 1328a and 1328b and proximal supports 1330a and 1330b, specifically vertical face 1378 and vertical face 1389.

In some examples, such as during a de-rotation procedure, more than one force may be applied to extensions 1306 and 1308 using, for example, a tool or one or more hands. During a de-rotation procedure, extensions 1306 and 1308 can be grasped and a force can be applied to extension 1306. For example, force F2 can be applied. Because a head of anchor 1300 can be secured to a vertebra, force F2 can create a bending moment on extension 1306. Further, during de-rotation, a force, such as force F4 can be applied to extension 1308 (at a position relatively lower than force F2), which can increase the moment about extensions 1306 and 1308. When a moment is created, asymmetric axial movement between extensions 1306 and 1308 can occur. In this example, the moment can create a resultant force that causes proximal translation of extension 1306 relative to extension 1308. However, as discussed above, because distal flat 1376 can contact distal flat 1388, relative proximal movement of extension 1306 to extension 1308 can be limited, which can help prevent undesired break-off of extension 1306 from the head by transferring load to extension 1308. This design can also help allow a greater moment to be applied to extensions 1306 and 1308 during a de-rotation procedure.

Distal ramp 1379 and distal ramp 1390 can converge together as they extend distally to substantially form an upside down V-shape from a front view with respect to FIGS. 13A and 13B. Though the ramps are discussed as having a V-shape, other shapes such as a U-shape can be used in other examples. This configuration can allow distal ramp 1379 and distal ramp 1390 to function as lead-ins (or lead-outs) for a connection member or rod and/or an insertion tool. That is, a connection member, which can have a cylindrical cross-section, can be removed through proximal supports 1328a and 1330a by being forced into distal ramp 1379 and distal ramp 1390.

For example, when it is desired to remove a connection member from channels 1320 (for example, to reposition the connection member), the connection member can be moved proximally within channels 1320 until the connection member engages distal ramp 1379 and distal ramp 1390. This engagement can transform the proximally directed forces into medial and lateral forces to cause extensions 1306 and 1308 to separate so that the connection member can be passed through proximal supports 1328a and 1328b and 1330a and 1330b and removed from anchor 1300.

Figure 14A:
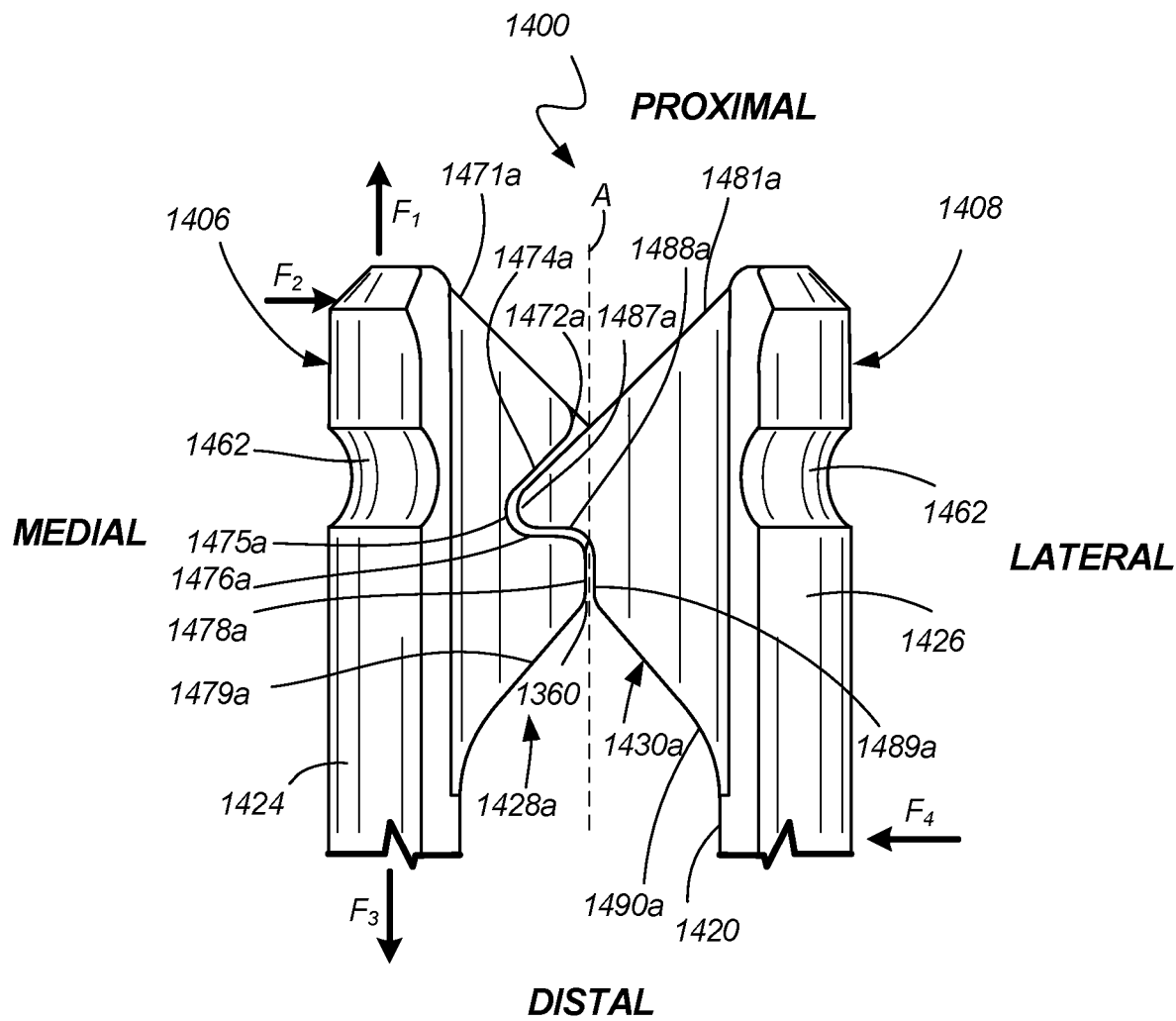
FIG. 14A illustrates a front view of an anchor with extended tabs, in accordance with at least one example of this disclosure.
Figure 14B:
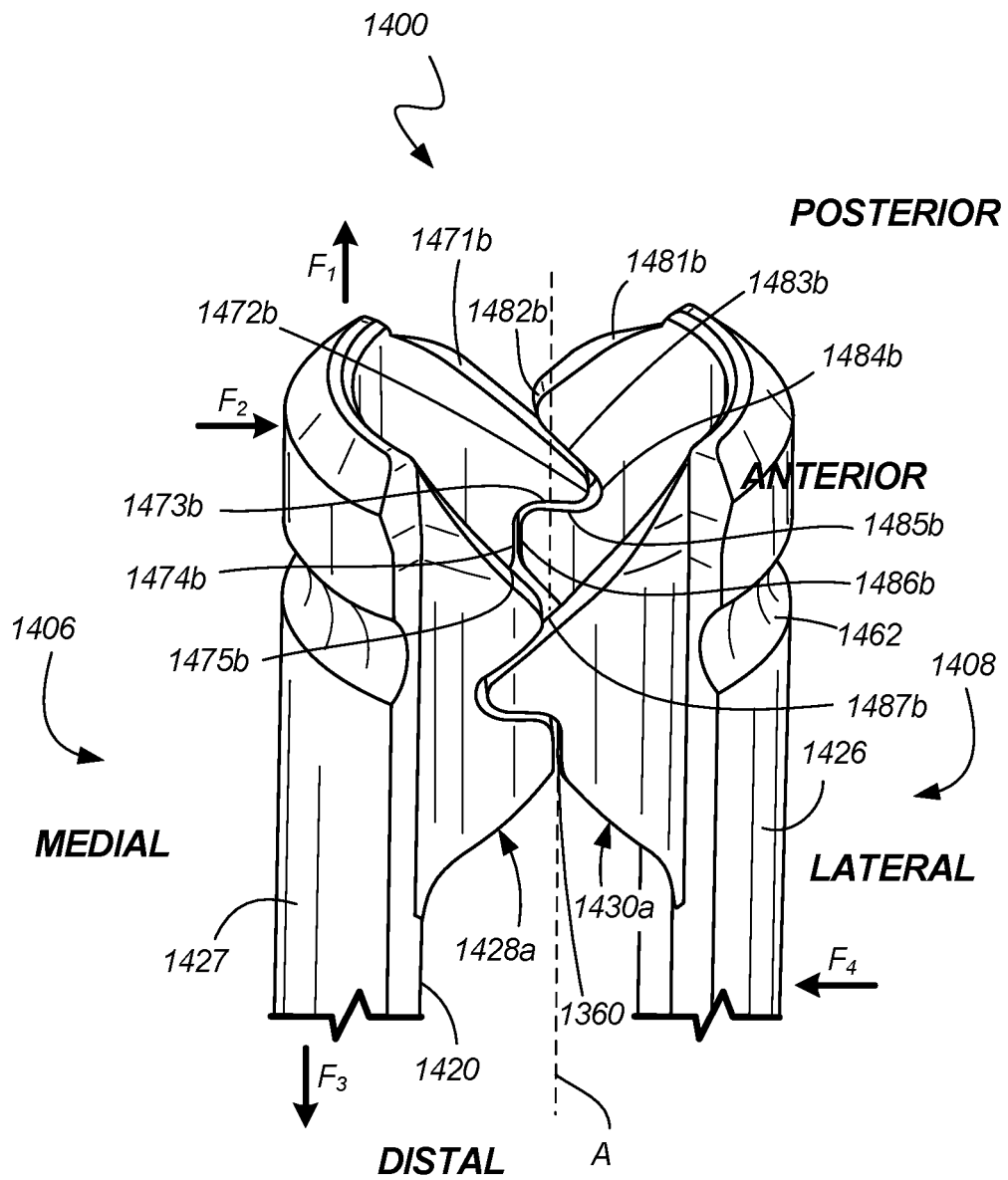
FIG. 14B illustrates an isometric front view of an anchor with extended tabs, in accordance with at least one example of this disclosure.

FIG. 14A illustrates a front view of anchor 1400 with extended tabs, in accordance with at least one example of this disclosure. FIG. 14B illustrates an isometric front view of anchor 1400 with extended tabs, in accordance with at least one example of this disclosure. Anchor 1400 can include interlocking proximal supports, where medial and lateral tabs can interlock without connecting and can contact each other in response to forces to limit relative movement of extended tabs to help limit accidental breakoff. Anchor 1400 can also include asymmetric proximal supports such that a posterior support is a mirror of an anterior support to help reduce a size of the proximal supports. Any of the previously discussed anchors can be modified to include asymmetric interlocking proximal supports. Anchor 1400 is discussed further below with respect to FIGS. 14A and 14B.

Anchor 1400 can include a head and extensions 1406 and 1408. Extension 1406 can include elongate portion 1424 and proximal supports 1428a and 1428b. Extension 1408 can include elongate portion 1426 and proximal supports 1430a and 1430b. Extensions 1406 and 1408 can be separated, distal of proximal supports 1428 and 1430, by channels 1420, and can also include groove 1462. Proximal support 1428a can include proximal ramp 1471a, proximal tongue 1472a, medial ramp 1474a, distal groove 1475a, distal flat 1476, vertical face 1478a, and distal ramp 1479. Proximal support 1428b can include proximal ramp 1471b, proximal tongue 1472b, distal flat 1473b, vertical face 1474b, and distal ramp 1475b.

Proximal support 1430a can include proximal ramp 1481a, distal tongue 1487a, distal flat 1488a, vertical face 1489a, and distal ramp 1490a. Proximal support 1430b can include proximal ramp 1481b, proximal tongue 1482b, medial ramp 1483b, distal groove 1484b, distal flat 1485b, vertical face 1486b, and distal ramp 1487b. Also shown in FIGS. 14A and 14B are axis A, forces F1, F2, F3, and F4, and orientation indicators Proximal, Distal, Medial, Lateral, Posterior and Anterior.

The portions of proximal supports 1428a, 1428b, 1430a, and 1430b can be connected similarly to those of proximal supports 1328a, 1328b, 1330a, and 1330b discussed above, except that, in this example proximal supports 1428a and 1430a can be asymmetric to proximal supports 1428b and 1430b, which can help allow each of proximal supports 1428a, 1428b, 1430a, and 1430b to be relatively smaller, as explained further below.

Proximal supports 1428a and 1430a can interact to help resist relative movement of extensions 1406 and 1408 in response to force F1 applied to extension 1406 while proximal supports 1428b and 1430b can interact to help resist relative movement of extensions 1406 and 1408 in response to force F3 applied to extension 1406. For example, distal flat 1476a and distal flat 1488a of proximal supports 1428a and 1430a can be configured to engage and transfer forces therebetween in response to force F1 (or movement in a direction of force F1) to limit relative translation of extension 1406 to extension 1408, while distal flat 1473b and distal flat 1485b of proximal supports 1428b and 1430b can be configured to engage and transfer forces therebetween in response to force F3 (or movement in a direction of force F3) to limit relative translation of extension 1406 to extension 1408. In this way, proximal supports 1428a and 1430a can transmit axial forces between extensions 1406 and 1408 in one direction and proximal supports 1428b and 1430b can transmit axial forces between extensions 1406 and 1408 in the opposite direction. That is, each set of proximal supports has only one set of flats, but together the set of proximal supports limits axial translation in both directions. This can help allow each of proximal supports 1428a, 1428b, 1430a, and 1430b to be relatively smaller (proximally to distally) in comparison to other supports that may include multiple sets of flats on each set of supports, which can help reduce cost.

In some examples, a force orthogonal to axis A can be applied to one or more extensions 1406 and 1408. For example, force F2 can be applied to extension 1406. In this example, the complimentary surfaces of proximal supports 1428a and 1428b and proximal supports 1430a and 1430b can contact each other to help limit pinching in. Though many portions of the proximal supports can be configured to contact each other to help limit pinching in, vertical faces 1478a and 1489a of proximal supports 1428a and 1430a can be configured such that vertical faces 1478b and 1489b of proximal supports 1428b and 1430b contact each other to transfer loads therebetween to limit pinching in and to limit bending of one extension (such as extension 1406) relative to the other (such as extension 1408).

Proximal ramps 1471 and 1481 and distal ramps 1479a, 1475b, 1490a, and 1487b can be configured to allow a connecting member to separate proximal supports 1428a and 1428b from proximal supports 1430a and 1430b during insertion and removal, respectively, of the connecting member, as discussed above with respect to anchor 1300. However, because each of proximal supports 1428a and 1428b and proximal supports 1430a and 1430b include fewer portions (because anterior proximal supports 1428a and 1430a are asymmetric to posterior proximal supports 1428b and 1430b) the connecting member can be more quickly and easily passed between proximal supports 1428a and 1428b from proximal supports 1430a and 1430b.

Figure 15A:
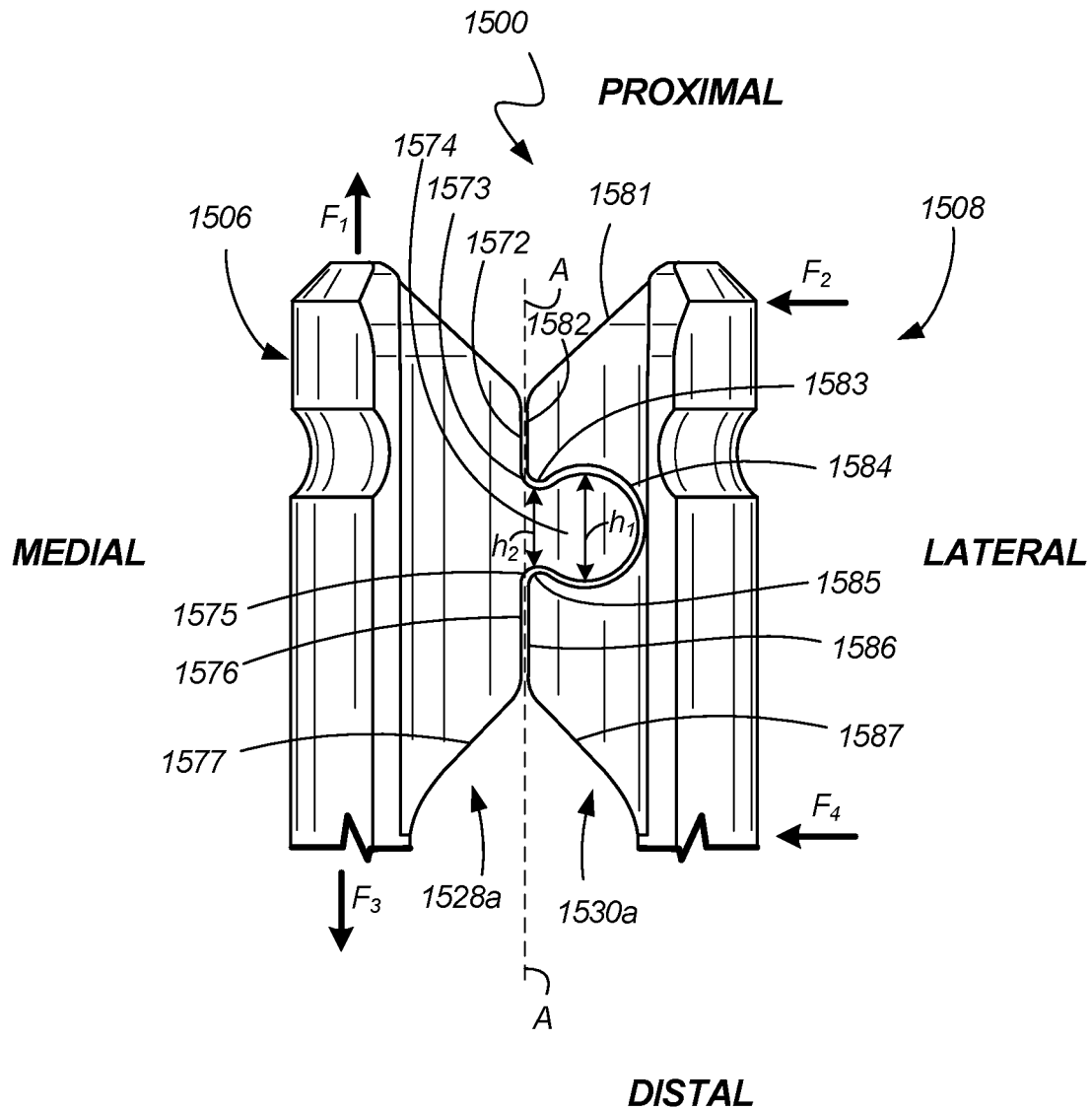
FIG. 15A illustrates a front view of an anchor with extended tabs, in accordance with at least one example of this disclosure.
Figure 15B:
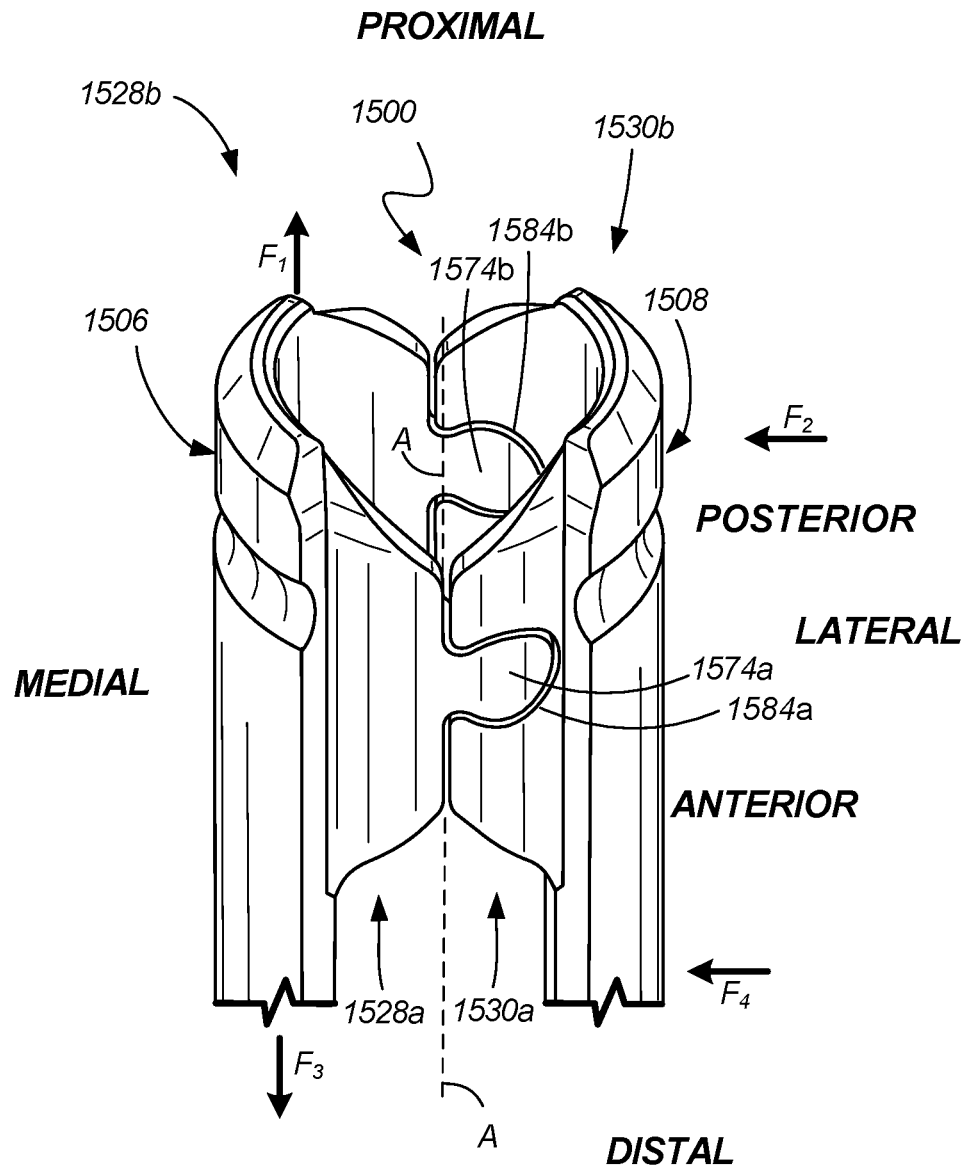
FIG. 15B illustrates an isometric front view of an anchor with extended tabs, in accordance with at least one example of this disclosure.

FIG. 15A illustrates a front view of anchor 1500 with extended tabs, in accordance with at least one example of this disclosure. FIG. 15B illustrates an isometric front view of anchor 1500 with extended tabs, in accordance with at least one example of this disclosure. Anchor 1500 can include proximal supports that can lock (or fit together in an interlocking manner) to limit unwanted separation of extended tabs, while still being separable to allow removal or break-off of the extended tabs from a head of anchor 1500. Any of the previously discussed anchors can be modified to include locking proximal supports. Anchor 1500 is discussed further below with respect to FIGS. 15A and 15B.

Anchor 1500 can include a head and extensions 1506 and 1508. Extension 1506 can include elongate portion 1524 and proximal supports 1528a and 1528b. Extension 1508 can include elongate portion 1526 and proximal supports 1530a and 1530b. Extensions 1506 and 1508 can be separated, distal of proximal supports 1528 and 1530, by channels 1520. Each of proximal supports 1528a and 1528b can include proximal ramp 1571, proximal vertical portion 1572a, proximal recess 1573, finger 1574, distal recess 1574, distal vertical portion 1575, distal vertical portion 1576, and distal ramp 1577. Each of proximal supports 1530a and 1530b can include proximal ramp 1581, proximal vertical portion 1582, proximal extension 1583, finger recess 1584, distal extension 1585, distal vertical portion 1586, and distal ramp 1587. Also shown in FIGS. 15A and 15B are forces F1, F2, F3, and F4, heights h1 and h2, and orientation indicators Proximal, Distal, Medial, Lateral, Anterior, and Posterior.

The components of proximal supports 1528 and 1530 can be connected such that proximal support 1528 locks with proximal support 1530 to help limit separation of extensions 1506 and 1508 and to help limit pinching in of extensions 1506 and 1508. More specifically, finger 1574 can be a projection extending laterally from between proximal recess 1573 and distal recess 1574, where finger 1574 has a maximum height h1 that is larger than height h2 between proximal recess 1573 and distal recess 1574.

Proximal recess 1573 and distal recess 1574 can be sized and shaped complimentary to proximal extension 1583 and distal extension 1585, respectively, such that proximal extension 1583 and distal extension 1585 can nest within proximal recess 1573 and distal recess 1574, respectively. Finger recess 1584 can be a recess extending into proximal support 1530 from between proximal extension 1583 and distal extension 1585 and can be sized and shaped substantially complimentary to finger 1574. In some examples, finger 1574 and recess 1584 can be substantially round or can have a substantially curved profile to allow a connection member to pass over and/or between finger 1574 and recess 1584.

Finger recess 1584 can be sized to receive finger 1574 therein. When finger 1574 is disposed therein, lateral movement of finger 1584 can be limited by contact between a lateral portion of finger 1574 with a lateral portion of finger recess 1584, such that finger 1574 is locked or interlocked to finger recess 1584. In some examples, finger 1574 can be disposed within finger recess 1584 similar to a puzzle piece engagement. In this engagement, lateral movement of extension 1506 can also be limited by contact between proximal vertical portion 1572 and proximal vertical portion 1582 and by contact between distal vertical portion 1576 and distal vertical portion 1586. Also, medial movement of finger 1574 can be limited by contact between a medial portion of finger 1574 and proximal extension 1583 and by contact between finger 1574 and distal extension 1585. This contact can help reduce medial movement of finger 1574 (and therefore proximal support 1528) relative to proximal support 1530 to help limit unwanted separation of extensions 1506 and 1508 to help reduced unwanted break-off of extensions 1506 and/or 1508 from the head of anchor 1500.

Further, engagement between a proximal portion of finger 1574 and recess 1584 can help limit proximal movement of extension 1506 relative to extension 1508 (such as caused by force F1) and contact between a distal portion of finger 1574 and recess 1584 can help limit distal movement of extension 1506 relative to extension 1508 (such as caused by force F3).

In operation of some examples, when separation of extension 1506 from extension 1508 from each other is desired, for example, to remove either of extension 1506 and 1508 from the head, either of extension 1506 and extension 1508 can be moved posteriorly or anteriorly (with respect to FIG. 15) relative to the other of extension 1506 and extension 1508 to disengage finger 1574 from finger recess 1584. For example, extension 1506 can be moved posteriorly relative to extension 1508 to move fingers 1574a and 1574b out of finger recesses 1584a and 1584b (respectively) so that extensions 1506 and/or 1508 can be moved medially and/or laterally relative to each other. This can allow one or more of extension 1506 and extension 1508 to be separated from a head or otherwise positioned as desired during a procedure.

Figure 16:
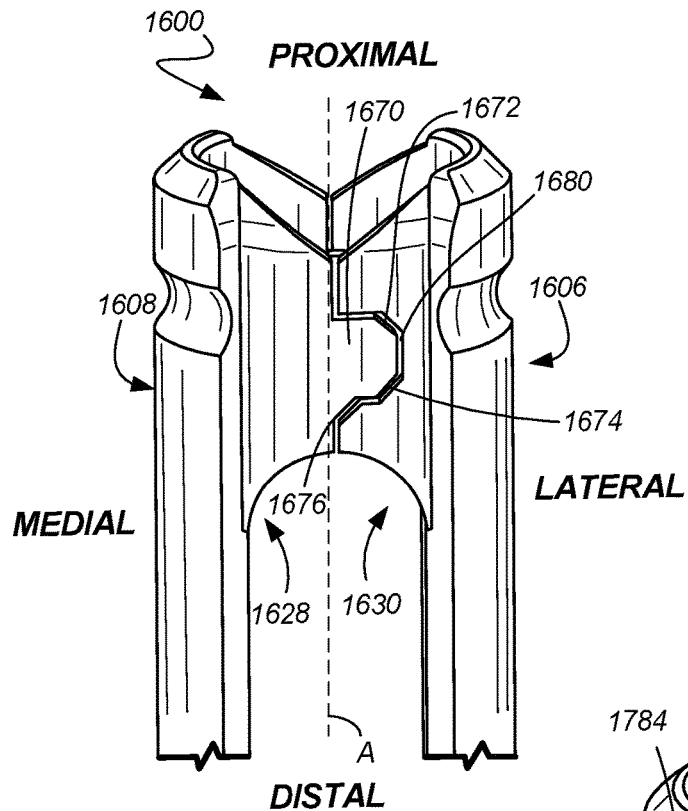
FIG. 16 illustrates an isometric front view of an anchor with extended tabs, in accordance with at least one example of this disclosure.

FIG. 16 illustrates an isometric front view of anchor 1600 with extended tabs, in accordance with at least one example of this disclosure. Anchor 1600 can include extensions 1606 and 1608. Extension 1606 can include proximal support 1628 and extension 1608 can include proximal support 1630. Extensions 1606 and 1608 can be separated, distal of proximal supports 1628 and 1630, by channels 1620. Proximal support 1628 can include finger 1670 including chamfers 1672, 1674, and 1676. Proximal support 1630 can include recess 1680. Also shown in FIG. 16 are axis A and orientation indicators Proximal, Distal, Medial, and Lateral.

Anchor 1600 can be similar to those discussed above, except that proximal supports 1628 and 1630 can include finger 1670 including chamfers 1672, 1674, and 1676 where recess 1680 can be sized and shaped complimentary to finger 1670 to receive finger 1670 therein. Chamfers 1672, 1674, and 1676 (along with vertical and horizontal portions of proximal supports 1628 and 1630) can help reduce pinching in of extensions 1628 and 1630 and can help limit relative translation of extensions 1628 and 1630, while chamfers 1672, 1674, and 1676 can help allow a connection member to be passed through proximal supports 1628 and 1630 without catching. In some examples, chamfers 1672, 1674, and 1676 may be less expensive to manufacture than other shapes while still helping to reduce friction and catching of a connection member as it passes between proximal supports 1628 and 1630.

Figure 17:
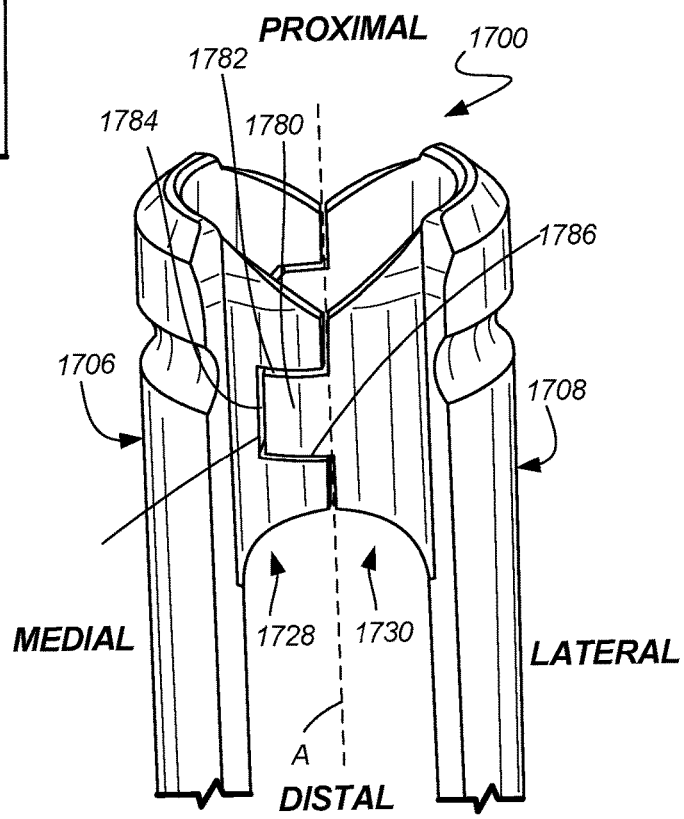
FIG. 17 illustrates an isometric front view of an anchor with extended tabs, in accordance with at least one example of this disclosure.

FIG. 17 illustrates an isometric front view of anchor 1700 with extended tabs, in accordance with at least one example of this disclosure. FIG. 17 illustrates an isometric front view of anchor 1700 with extended tabs, in accordance with at least one example of this disclosure. Anchor 1700 can include extensions 1706 and 1708. Extension 1706 can include proximal support 1728 and extension 1708 can include proximal support 1730. Extensions 1706 and 1708 can be separated, distal of proximal supports 1728 and 1730, by channels 1720. Proximal support 1728 can include recess 1770. Proximal support 1730 can include flat portions 1782, 1784, and 1786. Also shown in FIG. 17 are axis A and orientation indicators Proximal, Distal, Medial, and Lateral.

Anchor 1700 can be similar to those discussed above, except that proximal support 1730 can include finger 1780 which can be a substantially rectangular projection extending medially from proximal support 1730. Flat portions 1782, 1784, and 1786 can engage recess 1770 of proximal support 1728 can help reduce pinching in of extensions 1728 and 1730 and can help limit relative translation of extensions 1728 and 1730.

Figure 18:
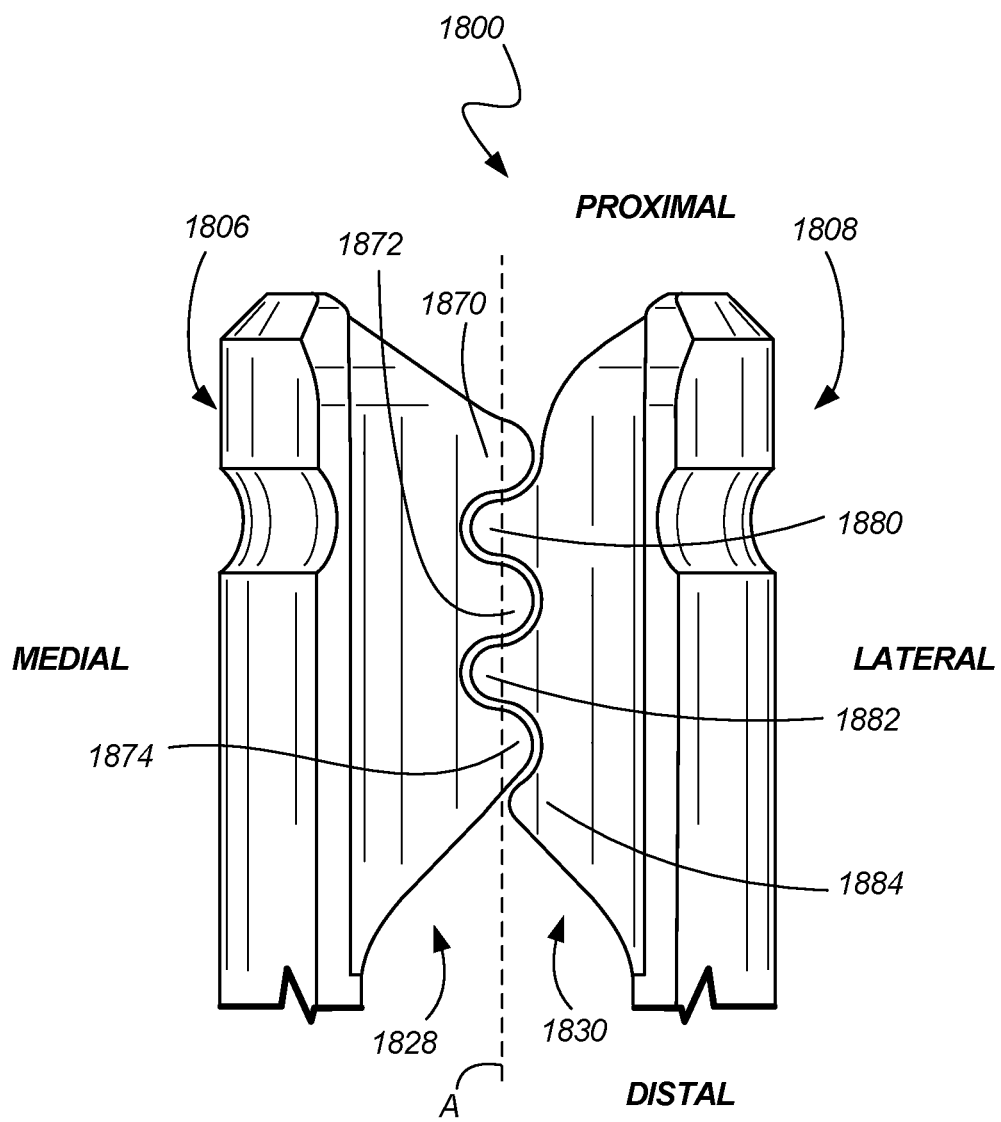
FIG. 18 illustrates a front view of an anchor with extended tabs, in accordance with at least one example of this disclosure.

FIG. 18 illustrates a front view of anchor 1800 with extended tabs, in accordance with at least one example of this disclosure. Anchor 1800 can include interlocking proximal supports having a constantly curving geometry (including no flat portions) to help reduce friction of a connection member passing between the proximal supports. Any of the previously discussed anchors can be modified to include constantly curving geometry.

Anchor 1800 can include extensions 1806 and 1808. Extension 1806 can include proximal support 1828 and extension 1808 can include proximal support 1830. Extensions 1806 and 1808 can be separated, distal of proximal supports 1828 and 1830, by channels 1820. Proximal support 1828 can include proximal finger 1870, medial finger 1872, and distal finger 1874. Proximal support 1830 can include proximal finger 1880, medial finger 1882, and distal finger 1884. Also shown in FIG. 18 are axis A and orientation indicators Proximal, Distal, Medial, and Lateral.

Proximal finger 1870, medial finger 1872, and distal finger 1874 of proximal support 1828 can interlock with proximal finger 1880, medial finger 1882, and distal finger 1884 of proximal support 1830 to help limit relative movement of extensions 1806 and 1808. Interlocking of the fingers of proximal support 1828 and proximal support 1830 can be similar to a finger joint arrangement, except that each portion of the fingers of proximal support 1828 and proximal support 1830 can have a continuously curving profile. That is, an outer portion of each of proximal finger 1870, medial finger 1872, and distal finger 1874 of proximal support 1828 and proximal finger 1880, medial finger 1882, and distal finger 1884 of proximal support 1830 can be without a flat portion, such that, together, the fingers form an interface having a snaking profile. This geometry and arrangement can help reduce friction or catching on a connection member when the connection member is passed between proximal supports 1828 and 1830. However, because each of proximal supports 1828 and 1830 includes three interlocking fingers, there can be a large contact area between proximal supports 1828 and 1830, which can help improve force transmission between proximal finger 1870, medial finger 1872, and distal finger 1874 of proximal support 1828 and proximal finger 1880, medial finger 1882, and distal finger 1884 of proximal support 1830 to help limit relative translation of extensions 1806 and 1808. Though three fingers of proximal supports 1828 and 1830 can provide a large contact area, less fingers (such as one or two) or more fingers (such as four, five, or the like) can be used in other examples.

Figure 19:
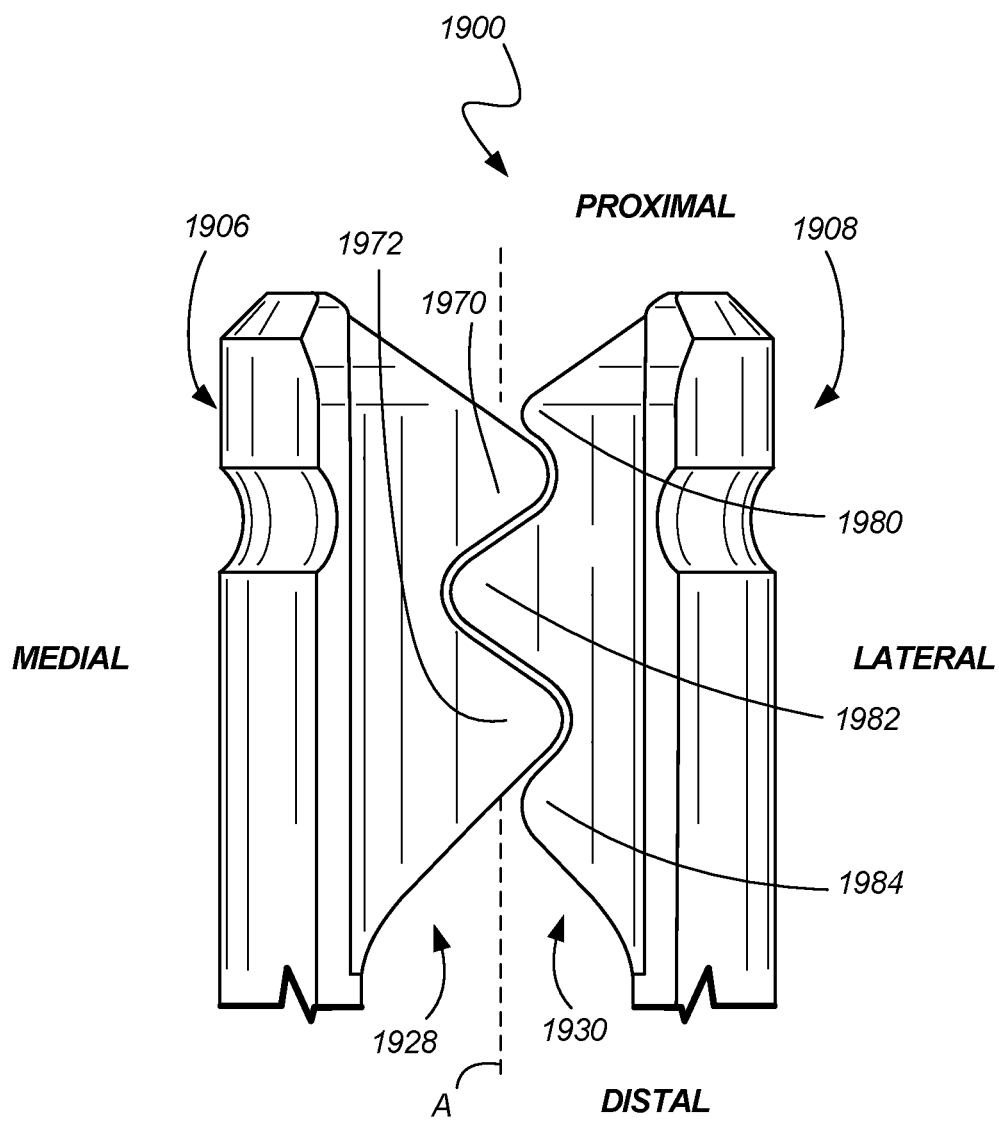
FIG. 19 illustrates a front view of an anchor with extended tabs, in accordance with at least one example of this disclosure.

FIG. 19 illustrates a front view of anchor 1900 with extended tabs, in accordance with at least one example of this disclosure. Anchor 1900 can include interlocking proximal supports having a curving geometry (including no axial flat portions or axially transverse flat portions) to help reduce friction of a connection member passing between the proximal supports. Any of the previously discussed anchors can be modified to include curving geometry.

Anchor 1900 can include extensions 1906 and 1908. Extension 1906 can include proximal support 1928 and extension 1908 can include proximal support 1930. Extensions 1906 and 1908 can be separated, distal of proximal supports 1928 and 1930, by channels 1920. Proximal support 1928 can include proximal finger 1970 and distal finger 1972. Proximal support 1930 can include proximal finger 1980, medial finger 1982, and distal finger 1984. Also shown in FIG. 19 are axis A and orientation indicators Proximal, Distal, Medial, and Lateral.

Proximal finger 1970 and distal finger 1972 of proximal support 1928 can interlock with proximal finger 1980, medial finger 1982, and distal finger 1984 of proximal support 1930 to help limit relative movement of extensions 1906 and 1908. Interlocking of the fingers of proximal support 1928 and proximal support 1930 can be similar to a finger joint arrangement, except that each portion of the fingers of proximal support 1928 and proximal support 1930 can have a curving profile termination with a straight portion connecting the curving terminations.

That is, a termination of each finger can be curved. For example, a lateral-most portion of proximal finger 1970 can be curved and can be connected to substantially straight portions on either side. However, the straight portions are not axially aligned (vertical with respect to FIG. 19) or axially tangential (horizontal with respect to FIG. 19). Further, each of proximal finger 1970 and distal finger 1972 can be separated by a recess configured to receive finger 1982, where the recess is sized and shaped complementary to finger 1982. This arrangement of proximal finger 1970, distal finger 1972, proximal finger 1980, medial finger 1982, and distal finger 1984 can form an interface having a substantially snaking profile. This geometry and arrangement can help reduce friction or catching on a connection member when the connection member is passed between proximal supports 1928 and 1930. However, because proximal support 1928 includes two interlocking fingers and proximal support 1930 includes three interlocking fingers, there can be a large contact area between proximal supports 1928 and 1930, which can help limit relative translation of extensions 1906 and 1908.

Figure 20A:
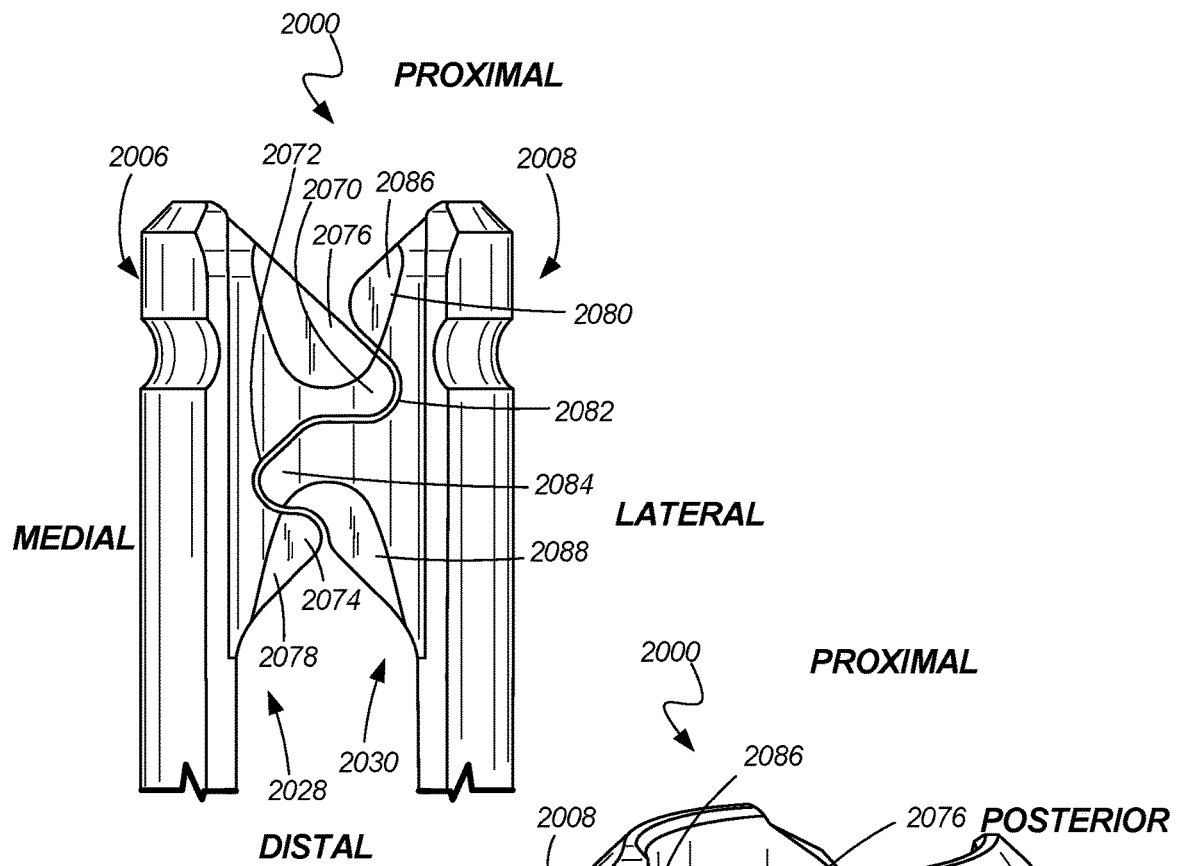
FIG. 20A illustrates a front view of an anchor with extended tabs, in accordance with at least one example of this disclosure.
Figure 20B:
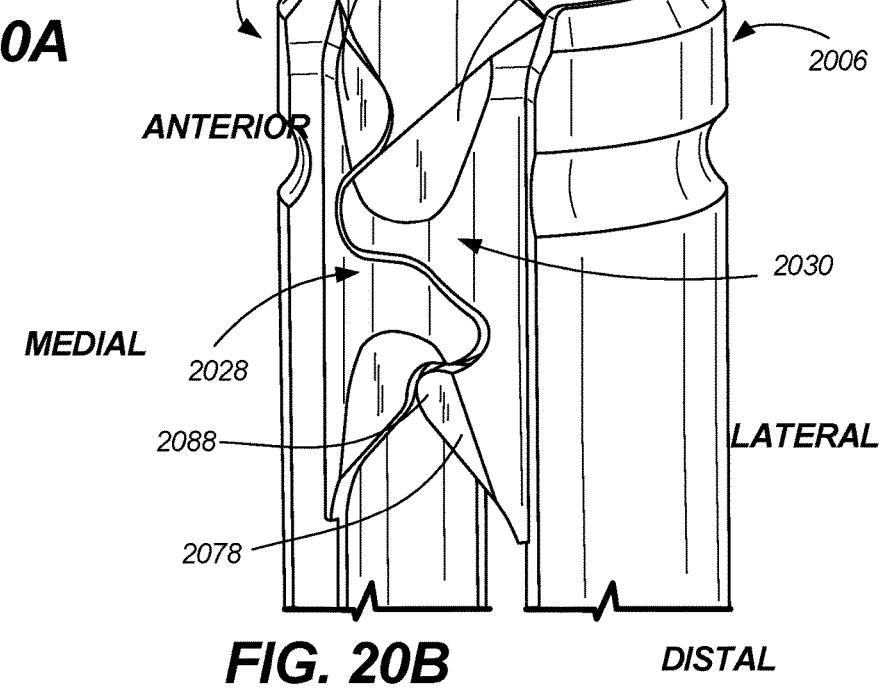
FIG. 20B illustrates an isometric view of an anchor with extended tabs, in accordance with at least one example of this disclosure.
Figure 20C:
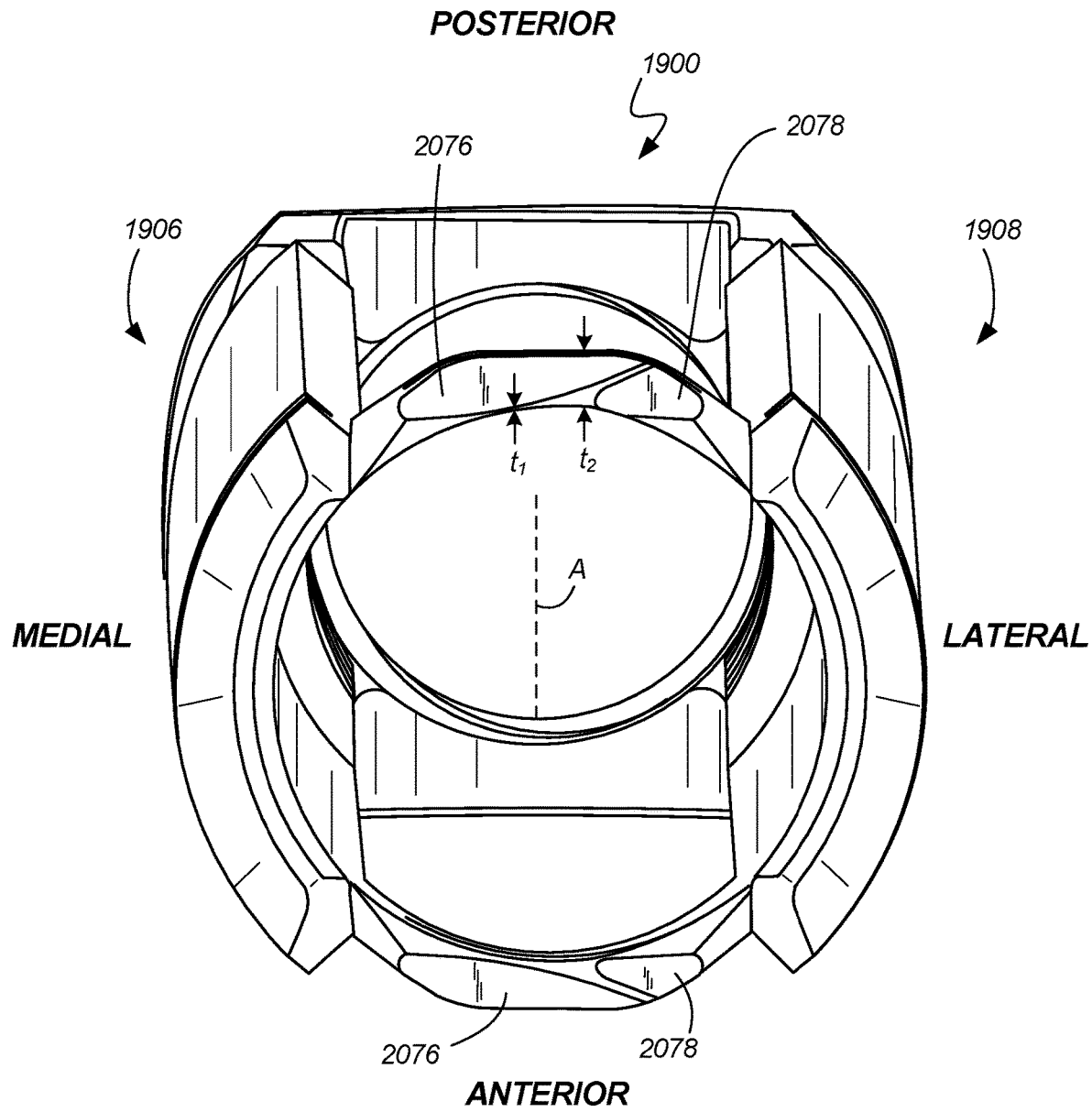
FIG. 20C illustrates an isometric top view of an anchor with extended tabs, in accordance with at least one example of this disclosure.
Figure 20D:
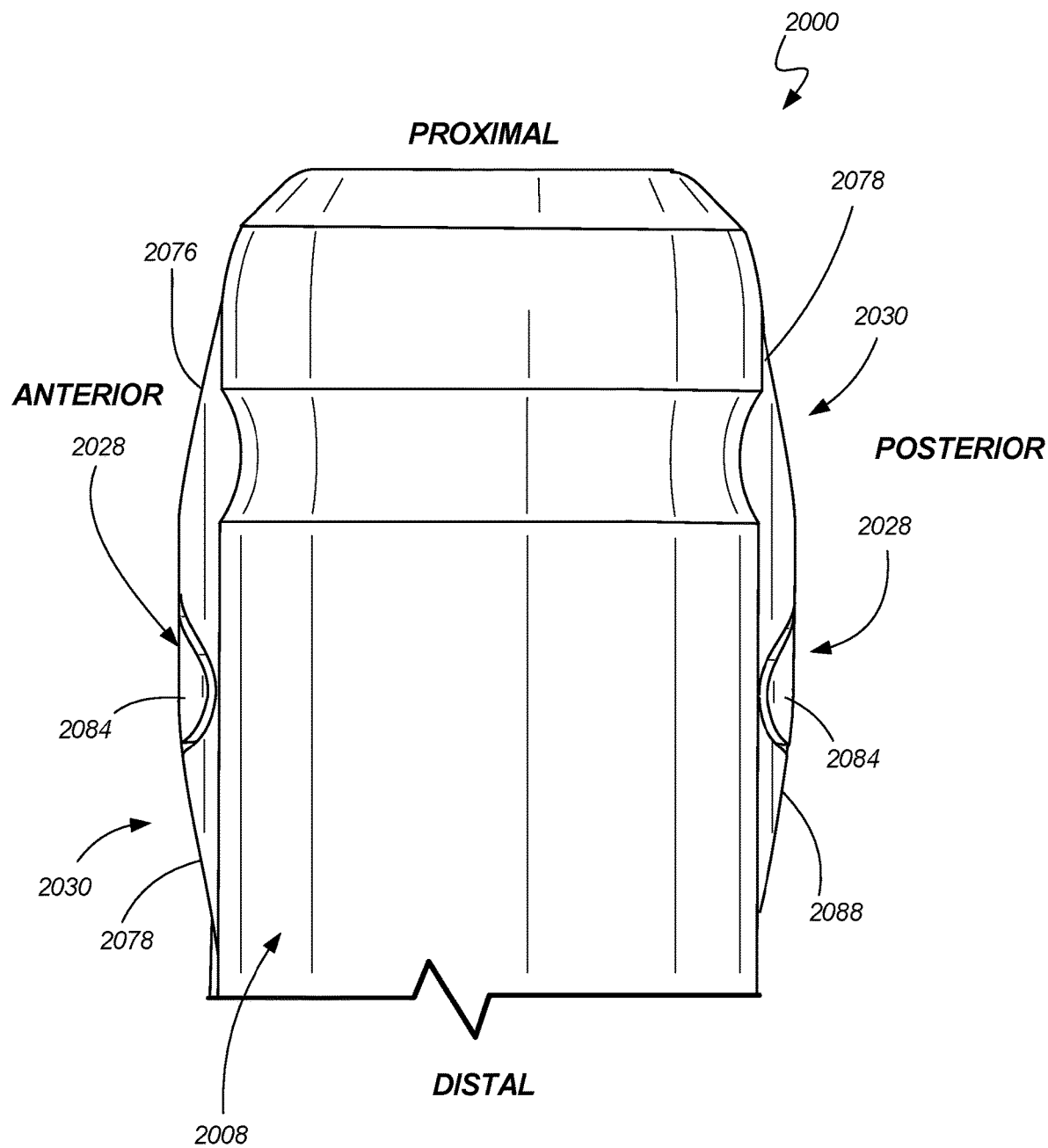
FIG. 20D illustrates an isometric side view of an anchor with extended tabs, in accordance with at least one example of this disclosure.

FIG. 20A illustrates a front view of anchor 2000 with extended tabs, in accordance with at least one example of this disclosure. FIG. 20B illustrates an isometric view of anchor 2000 with extended tabs, in accordance with at least one example of this disclosure. FIG. 20C illustrates an isometric top view of anchor 2000 with extended tabs, in accordance with at least one example of this disclosure. FIG. 20D illustrates an isometric side view of anchor 2000 with extended tabs, in accordance with at least one example of this disclosure. Anchor 2000 can include proximal supports having one or more chamfers extending proximally to distally and anteriorly to posteriorly on proximal and/or distal portions of the proximal supports to help guide insertion and removal of a connection member between the extended tabs through the proximal supports where the connection member is being inserted from the anterior or posterior with respect to FIG. 20B. Any of the previously discussed anchors can be modified to include chamfered proximal supports. Anchor 2000 is discussed in further detail below with respect to FIGS. 20A-20C.

Anchor 2000 can include extensions 2006 and 2008. Extension 2006 can include proximal support 2028 and extension 2008 can include proximal support 2030. Extensions 2006 and 2008 can be separated, distal of proximal supports 2028 and 2030, by channels 2020. Proximal support 2028 can include finger 2070, recess 2072, finger 2074, proximal chamfer portion 2076, and distal chamfer portion 2078. Proximal support 2030 can include finger 2080, recess 2082, finger 2084, proximal chamfer portion 2086, and distal chamfer portion 2088. Also shown in FIG. 20 are axis A, thicknesses t1 and t2, and orientation indicators Proximal, Distal, Medial, Lateral, Anterior, and Posterior.

Anchor 2000 can be connected similarly to anchors discussed above where finger 2070 of proximal support 2028 can extend into recess 2082 of proximal support 2030, and where recess 2082 can have a complimentary shape and sized to finger 2070 such that proximal support 2028 and 2030 interlock. Similarly, finger 2084 can extend medially from proximal support 2030 into recess 2072 of proximal support 2028. In these configurations, proximal supports 2028 and 2030 can help limit pinching in of extensions 2006 and extensions 2008 and can help limit axial relative translation of extensions 2006 and 2008 to help limit unwanted breakoff from a head of anchor 2000.

Proximal chamfer portion 2076 can be a chamfer in proximal finger 2072 which can have thickness t1 at a proximal end that is smaller than thickness t2, which can be a thickness of finger 2070 distal of the proximal portion (t2). That is, proximal chamfer 2076 portion can begin at a proximal beginning of finger 2070 and can extend distally therefrom. Similarly, proximal chamfer portion 2076 can be a chamfer in proximal finger 2080 which can have thickness t1 at a proximal end that is smaller than thickness t2, which can be a thickness of finger 2080 distal of the proximal portion.

Distal chamfer portion 2078 and distal chamfer portion 2088 can be the opposite of proximal chamfer portions 2076 and 2086, where each of distal chamfer portion 2078 and distal chamfer portion 2088 begin at a distal portion of proximal supports 2028 and 2030, respectively, and increase in thickness as they extend proximally. In some examples, proximal chamfer portions 2076 and 2086 can have a substantially U-shape from an anterior perspective (as shown in FIG. 20A) and distal chamfer portions 2078 and 2088 can have a substantially upside-down U-shape from an anterior perspective (as shown in FIG. 20A). In other examples, proximal chamfer portions 2076 and 2086 can have other shapes, such as V, or the like. In some examples, proximal chamfer portions 2076 and 2086 and distal chamfer portions 2078 and 2088 can form mirrors of the same shape and in other examples, proximal chamfer portions 2076 and 2086 and distal chamfer portions 2078 and 2088 can have different shapes and different sizes.

In operation of some examples, where it is desired to insert a connection member into channels of anchor 2000 between extensions 2006 and 2008 for reduction into a head of the anchor, it may be preferable or necessary to insert the connection member into anchor 2000 at an angle. Because the connection member must pass between proximal supports 2028 and 2030, it may be difficult to insert the connection member between proximal supports 2028 and 2030 in a direction not parallel to axis A. The example of FIG. 20 addresses this issue by including chamfers proximal chamfers 2076 and 2086 and distal chamfers 2078 and 2088.

Because proximal chamfer portions 2076 and 2086 have a reduced thickness t1 at a proximal portion, a connection member can be inserted in a direction not parallel to axis A. For example, the connection member can engage proximal chamfer portions 2076 and 2086 oriented at an angle of 75 degrees from axis A (an axis of the connection member can be approximately 75 degrees from axis A). Because proximal chamfer portions 2076 and 2086 reduce in thickness towards the proximal side of proximal supports 2028 and 2030, proximal chamfer portions 2076 and 2086 can be a lead in for insertion in this direction, where proximal chamfer portions 2076 and 2086 direct the connection members radially inward and partially distally as the connection member separates proximal supports 2028 and 2030 to enter channels 2030. Similarly, distal chamfer portions 2078 and 2088 can help guide removal of the connection member from channels 1230 from a direction not parallel to axis A (an axis of the connection member is at an angle not perpendicular to axis A). Though insertion of the connection member is discussed at an angle of 75 degrees, insertion at other angles is possible and proximal supports 2028 and 2030 can be configured to accept insertion at angles greater than 75 degrees.

Figure 21:
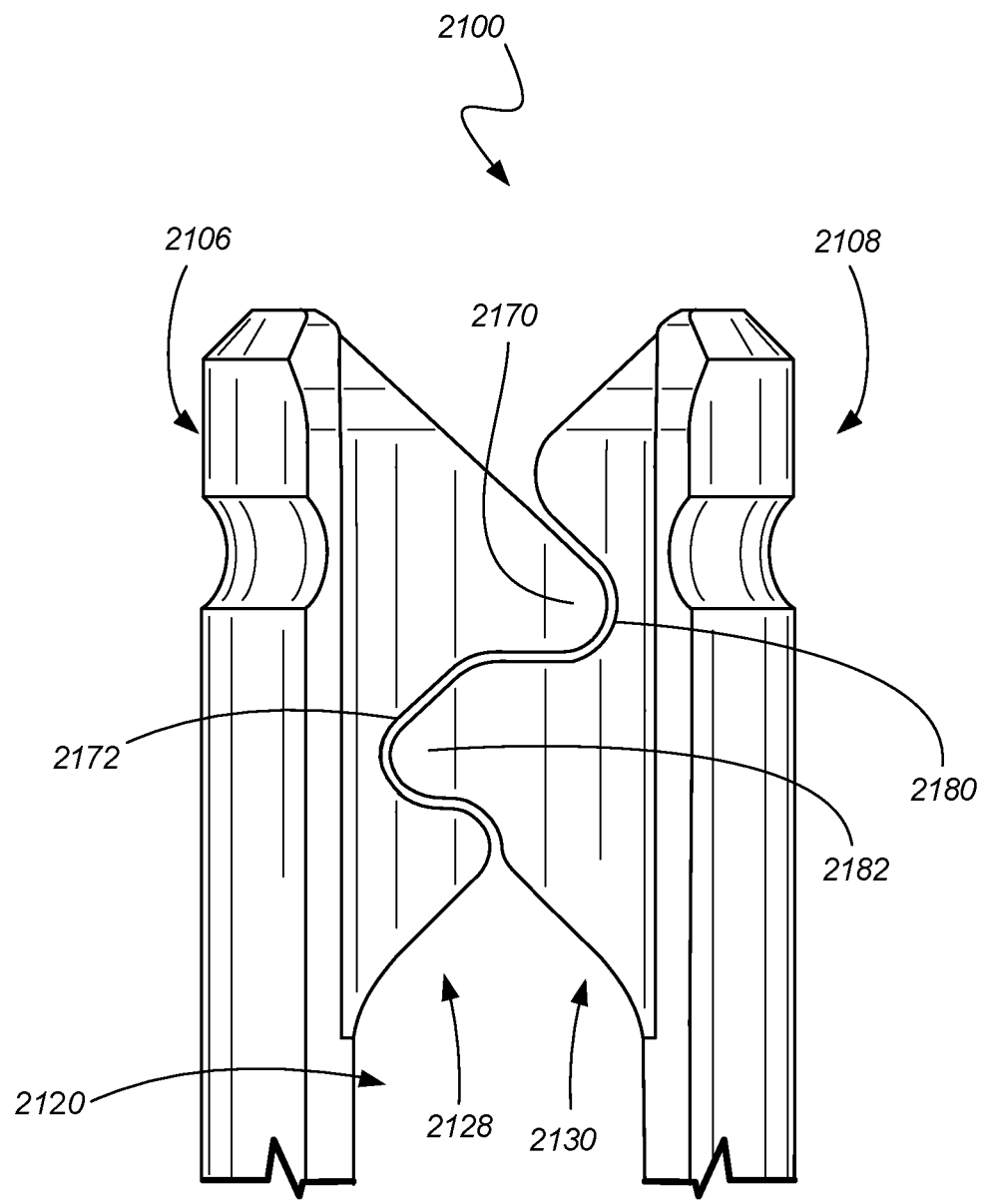
FIG. 21 illustrates a front view of an anchor with extended tabs, in accordance with at least one example of this disclosure.

FIG. 21 illustrates a front view of anchor 2100 with extended tabs, in accordance with at least one example of this disclosure. Anchor 2100 can include extensions 2106 and 2108. Extensions 2106 and 2108 can be separated, distal of proximal supports 2128 and 2130, by channels 2120. Extension 2106 can include proximal supports 2128 and extension 2108 can include proximal supports 2130. Proximal support 2128 can include finger 2170 and recess 2172. Proximal support 2130 can include recess 2180 and finger 2182.

Anchor 2100 can be similar to anchor 1300 discussed above, except that the curves of anchor 2100 (finger 2170 and 2182 and recesses 2180 and 2172, for example) can have relatively larger radii of curvature. This can help reduce catching of a connection member that is being inserted into or removed from channels 2120 as the connection member passes between proximal supports 2128 and 2130.

NOTES AND EXAMPLES

The following, non-limiting examples, detail certain aspects of the present subject matter to solve the challenges and provide the benefits discussed herein, among others.

Example 1 is an anchor coupleable to a bone, the anchor comprising: a head including distal head portion and a proximal head portion, the proximal head portion open at a proximal end of the head; a shank extending distally from the distal head portion, the shank including a threaded portion configured to engage the bone; a first extension comprising: a first breakaway portion coupling the first extension to the proximal head portion, the first extension separable from the head at the first breakaway portion; a first elongate portion extending from a first end proximate the first breakaway portion to a second end along a longitudinal axis of the anchor, the first elongate portion including a length sufficient to extend the second end outside an incision when the shank is engaged in the bone; and a first proximal support coupled to the second end of the first elongate portion, the proximal support extending transverse to the longitudinal axis; and a second extension opposing the first extension, the second extension comprising: a second breakaway portion coupling the second extension to the proximal head portion, the second extension separable from the head at the second breakaway portion; a second elongate portion extending from a first end proximate the first breakaway portion to a second end along a longitudinal axis of the anchor, the first elongate portion including a length sufficient to extend the second end outside an incision when the shank is engaged in the bone; and a second proximal support coupled to the second end of the first elongate portion, the proximal support extending transverse to the longitudinal axis, the first proximal support portion and the second proximal support portion separated in a first condition and engaged to transfer forces there between in a second condition; and wherein the first and second extensions comprise a threaded portion on internal faces of the first and second extensions, the threaded portion extending distally from the first and second extensions into the head portion.

In Example 2, the subject matter of Example 1 optionally includes wherein the head includes a first side and a second side each open to substantially form a u-shape adapted to receive a connecting rod.

In Example 3, the subject matter of any one or more of Examples 1-2 optionally include wherein the first proximal support portion further comprises a first pair of arms extending transversely to the longitudinal axis of the anchor toward the second proximal support, and wherein the second proximal support portion further comprises a second pair of arms extending transversely to the longitudinal axis of the anchor toward the first proximal support.

In Example 4, the subject matter of Example 3 optionally includes wherein the first pair of arms comprises a first arm and a second arm and the second pair of arms comprises a third arm and a fourth arm, the first arm and the third arm separated in the first condition and engaged to transfer forces there between in the second condition.

In Example 5, the subject matter of Example 4 optionally includes wherein the first arm and second arm together with the first elongate portion form a first substantially c-shape and wherein the third arm and the fourth arm together with the second elongate portion form a second substantially c-shape larger than the first substantially c-shape.

In Example 6, the subject matter of Example 5 optionally includes wherein the first substantially c-shape is nestable within the second substantially c-shape.

In Example 7, the subject matter of any one or more of Examples 4-6 optionally include wherein the first arm terminates at a first end, the second arm terminates at a second end, the third arm terminates a third end proximate the first end, and the fourth arm terminates at a fourth end proximate the second end.

In Example 8, the subject matter of Example 7 optionally includes wherein the third arm comprises an undercut proximate the third end and the fourth arm comprises an undercut proximate the fourth end, the first end and second end nestable in the undercuts of the third end and fourth end, respectively.

In Example 9, the subject matter of any one or more of Examples 7-8 optionally include wherein the first end includes a first face, the second end includes a second face, the third end includes a third face, and the fourth end includes a fourth face, the first and third faces separated by a gap in the first condition and engageable in the second condition, and the second and fourth faces separated by a second gap in the first condition and engageable in the second condition.

In Example 10, the subject matter of Example 9 optionally includes wherein first face and second face are coplanar along a first plane and the third face and fourth face are coplanar along a second plane, the first and second planes substantially parallel with each other and with a diameter through the longitudinal axis.

In Example 11, the subject matter of Example 10 optionally includes wherein the first face and the third face are substantially parallel with each other in the first condition and the second face and the fourth face are substantially parallel with each other in the first condition.

In Example 12, the subject matter of Example 11 optionally includes wherein the first face and third face are parallel to a first plane and the second face and the fourth face are parallel to a second plane, the first and second planes substantially parallel with different chords transverse to the longitudinal axis.

In Example 13, the subject matter of any one or more of Examples 7-12 optionally include wherein the first and second ends include an increased cross-section to the third and fourth ends.

Example 14 is an anchor coupleable to a bone, the anchor comprising: a head including distal head portion and a proximal head portion, the proximal head portion open at a proximal end of the head; a shank extending distally from the distal head portion, the shank including a threaded portion configured to engage the bone; a first extension extending from a first Breakaway portion coupling the first extension to the proximal head portion, the first extension forming a first semi-cylindrical wall sharing a longitudinal axis with the head and including a length extendable beyond an incision when the shank is engaged in the bone, the first extension comprising: a first support coupled to a proximal end of the first semi-cylindrical wall, the first support extending transverse to the longitudinal axis; and a second extension extending from a second Breakaway portion coupling the second extension to the proximal head portion, the second extension forming a second semi-cylindrical wall sharing the longitudinal axis with the head and including a length extendable beyond an incision when the shank is engaged in the bone, the second extension comprising: a second support coupled to a proximal end of the second semi-cylindrical wall, the second support extending transverse to the longitudinal axis, the first support and the second proximal support separate and engageable to transfer forces there between.

In Example 15, the subject matter of Example 14 optionally includes wherein the first breakaway portion includes a thickness that is smaller than a thickness of the first semi-cylindrical wall.

In Example 16, the subject matter of any one or more of Examples 14-15 optionally include wherein the first semi-cylindrical wall and the second semi-cylindrical wall together substantially have a geometric shape of a hollow cylinder about the longitudinal axis, the first semi-cylindrical wall and the second semi-cylindrical wall separated by a pair of longitudinally extending slots configured to receive a connecting member therethrough.

In Example 17, the subject matter of any one or more of Examples 14-16 optionally include wherein the first support comprises a first arm terminating at a first end and a second arm terminating at a second end, and wherein the second support comprises a third arm terminating at a third end and a fourth arm terminating at a fourth end.

In Example 18, the subject matter of Example 17 optionally includes wherein the first end includes a first notch configured to receive the third end and the second end includes a second notch configured to receive the fourth end, wherein the notch and second notch each include an outer sidewall extension radially overlapping respective portions of the third and fourth arms.

Example 19 is an implant system for securing an anchor to a bone, the system comprising: an anchor comprising: a head open at a proximal end of the head; a shank extending distally from the head, the shank including a threaded portion configured to engage the bone; a first extension extending from a first Breakaway portion coupling the first extension to the proximal head portion, the first extension forming a first semi-cylindrical wall sharing a longitudinal axis with the head and including a first support coupled to a proximal end of the first semi-cylindrical wall, the first support extending transverse to the longitudinal axis, the first extension including a recess on an outer surface; a second extension extending from a second Breakaway portion coupling the second extension to the proximal head portion, the second extension forming a second semi-cylindrical wall sharing the longitudinal axis with the head and including a second support coupled to a proximal end of the second semi-cylindrical wall, the second support extending transverse to the longitudinal axis toward the first support, the first and second extensions separated by first and second extension slots configured to receive a connecting member therethrough; a sleeve adapted to reinforce the anchor, the sleeve comprising: a first sleeve arm and a second sleeve arm together extending longitudinally to form a longitudinal bore open at a distal end of the sleeve to receive the first extension and the second extension therein, the first and second sleeve arms separated by first and second sleeve slots alignable with the first and second extension slots to receive the connecting member therethrough; and an actuator disposed on an outer surface of one of the first and second sleeve arms, the actuator engageable with the recess of the first extension to restrict movement of the anchor relative to the sleeve, the actuator actuatable to release the sleeve from the anchor.

In Example 20, the subject matter of Example 19 optionally includes wherein the sleeve is sized to limit relative movement of the first and second extensions.

In Example 21, the subject matter of any one or more of Examples 19-20 optionally include a proximal portion coupling the first sleeve arm and the second sleeve arm proximate a proximal termination of the first sleeve arm and the second sleeve arm.

In Example 22, the subject matter of any one or more of Examples 19-21 optionally include the proximal portion further comprising: a projection extending radially inward from the proximal portion to engage a proximal end of one of the first semi-cylindrical wall and second semi-cylindrical wall, the projecting limiting axial translation of the anchor relative to the sleeve.

In Example 23, the apparatuses or method of any one or any combination of Examples 1-22 can optionally be configured such that all elements or options recited are available to use or select from.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. An anchor coupleable to a bone, the anchor comprising:
a head including distal head portion and a proximal head portion, the proximal head portion open at a proximal end of the head;
a shank extending distally from the distal head portion, the shank including a threaded portion configured to engage the bone;
a first extension extending from a first breakaway portion coupling the first extension to the proximal head portion, the first extension forming a first semi-cylindrical wall extending parallel to a longitudinal axis with the head and including a length extendable beyond an incision when the shank is engaged in the bone, the first extension comprising:
a first support coupled to a proximal end of the first semi-cylindrical wall, the first support extending transverse to the longitudinal axis, the first support including a first arm terminating at a first arm end and a second arm terminating at a second arm end; and
a second extension extending from a second breakaway portion coupling the second extension to the proximal head portion, the second extension forming a second semi-cylindrical wall extending parallel to the longitudinal axis with the head and including a length extendable beyond an incision when the shank is engaged in the bone, the second extension comprising:
a second support coupled to a proximal end of the second semi-cylindrical wall, the second support extending transverse to the longitudinal axis, the second support including a third arm terminating at a third arm end and a fourth arm terminating at a fourth arm end, the first support and the second proximal support separate and engageable to transfer forces there between, wherein the first arm end includes a first notch configured to receive the third arm end and the second arm end includes a second notch configured to receive the fourth end, wherein the first notch and the second notch each include an outer sidewall extension radially overlapping respective portions of the third and fourth arms such that a largest outer diameter of the first semi-cylindrical wall is greater than a largest outer diameter of the second semi-cylindrical wall.

2. The anchor of claim 1, wherein the first breakaway portion includes a thickness that is smaller than a thickness of the first semi-cylindrical wall.

3. The anchor of claim 2, wherein the first semi-cylindrical wall and the second semi-cylindrical wall together substantially have a geometric shape of a hollow cylinder about the longitudinal axis, the first semi-cylindrical wall and the second semi-cylindrical wall separated by a pair of longitudinally extending slots configured to receive a connecting member therethrough.

* * * * *